(12) United States Patent
Cousins et al.

(10) Patent No.: US 6,458,784 B1
(45) Date of Patent: Oct. 1, 2002

(54) VITRONECTIN RECEPTOR ANTAGONISTS

(75) Inventors: Russell Donovan Cousins, Oxford, PA (US); Richard McCulloch Keenan, Malvern, PA (US); Chet Kwon, King of Prussia, PA (US); William Henry Miller, Schwenksville, PA (US); Irene Nijole Uzinskas, Villanova, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/679,982

(22) Filed: Oct. 5, 2000

Related U.S. Application Data

(63) Continuation of application No. 09/482,647, filed on Nov. 10, 1998, now abandoned, which is a continuation of application No. 08/765,753, filed as application No. PCT/US95/08146 on Jun. 29, 1995.

(51) Int. Cl.[7] ............ A61K 31/55; C07D 243/14; C07D 285/36
(52) U.S. Cl. .............. 514/221; 514/221; 514/219; 514/213; 540/504; 540/512; 540/513; 540/514
(58) Field of Search .................. 540/504, 512, 540/513, 514; 514/221, 213

(56) References Cited

U.S. PATENT DOCUMENTS

| | | | |
|---|---|---|---|
| 4,297,346 A | 10/1981 | Rips et al. | |
| 4,322,346 A | 3/1982 | Korosi et al. | |
| 4,327,026 A | 4/1982 | Branca et al. | |
| 4,361,511 A | 11/1982 | Branca et al. | |
| 4,377,522 A | 3/1983 | Branca et al. | |
| 4,410,520 A | 10/1983 | Watthey et al. | |
| 4,497,740 A | 2/1985 | Zeugner et al. | |
| 4,604,389 A | 8/1986 | Reiffen et al. | |
| 4,737,495 A | 4/1988 | Bomhard et al. | |
| 4,808,713 A | 2/1989 | Attwood et al. | |
| 4,820,834 A | 4/1989 | Evans et al. | |
| 5,008,263 A | 4/1991 | Cooper et al. | 514/221 |
| 5,017,571 A | 5/1991 | Hansen et al. | |
| 5,043,447 A | 8/1991 | Pascal et al. | |
| 5,059,688 A | 10/1991 | Effland et al. | |
| 5,096,900 A | 3/1992 | George et al. | |
| 5,149,699 A | 9/1992 | Ellingboe et al. | |
| 5,241,065 A | 8/1993 | Berger et al. | |
| 5,250,679 A | 10/1993 | Blackburn et al. | |
| 5,403,836 A | 4/1995 | Blackburn et al. | |
| 5,438,118 A | 8/1995 | Callahan et al. | |
| 5,470,849 A | 11/1995 | Callahan et al. | |
| 5,565,449 A | 10/1996 | Blackburn et al. | |
| 5,663,166 A | 9/1997 | Blackburn et al. | |
| 5,674,863 A * | 10/1997 | Blackburn et al. | 514/211 |
| 5,674,865 A | 10/1997 | Blackburn et al. | |
| 5,693,636 A * | 12/1997 | Bondinell et al. | 514/221 |
| 5,939,412 A * | 8/1999 | Bondinell et al. | 514/213 |
| 6,008,214 A * | 12/1999 | Kwon et al. | 514/211 |
| 6,117,866 A * | 9/2000 | Bondinell et al. | 514/221 |
| 6,127,359 A * | 10/2000 | Bondinell et al. | 514/211 |
| 6,274,577 B1 * | 8/2001 | Brown et al. | 514/221 |

FOREIGN PATENT DOCUMENTS

| | | | |
|---|---|---|---|
| DE | 3702755 | 8/1988 | |
| EP | 045 451 | 2/1982 | |
| EP | 048 045 | 3/1982 | |
| EP | 167 920 | 1/1986 | ............ 540/570 |
| EP | 275 748 | 7/1988 | |
| EP | WO 89/05150 | 6/1989 | |
| EP | 341 915 | 11/1989 | |
| EP | 372 486 | 6/1990 | |
| EP | 381 033 | 8/1990 | |
| EP | 447 857 | 9/1991 | |
| EP | 478 328 | 4/1992 | |
| EP | 478 362 | 4/1992 | |
| EP | 478 363 | 4/1992 | |
| EP | 479 481 | 4/1992 | |
| EP | 512 829 | 11/1992 | |
| EP | 523 845 | 1/1993 | |
| WO | WO 92/07568 | 5/1992 | |
| WO | WO 92/09297 | 6/1992 | |
| WO | WO 93/00095 | 1/1993 | |
| WO | WO 93/08174 | 4/1993 | |
| WO | WO 94/14776 | 7/1993 | |
| WO | WO 94/11360 | 5/1994 | |
| WO | WO 94/14776 | 7/1994 | |
| WO | WO 96/00574 | 1/1996 | |

OTHER PUBLICATIONS

Sternbach, L.H., *J. Med. Chem.*, 22, 2 (1979).

Friedinger, R.M., Cholecystokinin and Gastrin Antagonists, *Med. Res. Rev.*, 9, 271 (1989).

Mori et al., New Synthesis of Diazepinone Skeleton Using Catalyzed Carbonylation, *Heterocycles*, 16 (1981).

Muller et al., Synthese von, 1, 2–annelierten 1, 4–Benzodiazepinen und 4, 1–Benzoxazepinen, *Helv. Chim. Acta*, 65, 2118 (1982).

(List continued on next page.)

*Primary Examiner*—Sabiha Qazi
(74) *Attorney, Agent, or Firm*—Mary E. McCarthy; Stephen Venetianer; Charles M. Kinzig

(57) ABSTRACT

Pharmaceutically active benzodiazapine compounds of formula (I) are disclosed. These compounds inhibit the vitronectin receptor and are useful for treatment of osteoporosis.

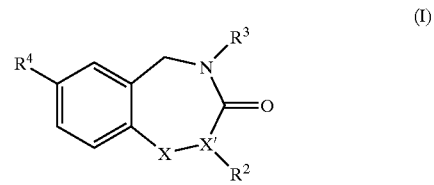

8 Claims, No Drawings

OTHER PUBLICATIONS

Heindel et al., Synthesis, Transformation and General Pharmacologic Activity in 1,4–Benzodiazepine–3,5–Diones, *J. Med. Chem.*, 14, 1233 (1971).

Pauwells et al., Potent and Selective Inhibition of HIV–1 Replication in vitro by a Novel Series of TIBO Derivatives, *Nature*, 343, 470 (1990).

Nichols et al., *J. Pharm. Exp. Ther.*, 270, 614 (1994).

Coller, *Coronary Artery Disease*, 3, 1016 (1992).

Topel et al. *Thrombosis and Haemostasis*, 70, 94 (1993).

Nichols et al., *TIPS*, 13, 413 (Nov. 1991).

Tighneanu et al., Double Cyclisation of Phenyglycine–o–carboxylic Acids–I, *Tetrahedron*, 36, 1385 (1980).

Callahan et al., *Peptide Chemistry 1992: Proceedings of the 2nd Japanese Symposium on Peptides Chemistry*, p. 495 (1993).

Tidwell et al., *Thrombosis Research*, vol. 19, pp. 339–349 (1980).

Samanen, et al., J. Med. Chem, 1996, vol. 39, No. 25, pp. 4867–4870.

Bondinell et al., Bioorganic and Medicinal Chemistry, vol. 2, No. 9, issued, 1994, "Design of a potent and orally active nonpeptide platelet fibrinogen receptor (GPIIb/IIIa) antagonist", pages.

Miller, et al. Tetrahedron Letters, vol. 36, Numer 3, issued 1995, "Synthesis of a 2–Benzazepine Analog of a Potent, Nonpeptide GPIIb/IIIa Antagonist", pp. 373–376.

Ku et al. Journal of Medicinal Chemistry, vol. 38, No. 1, issued Jan. 1995, "Potent Non–peptide Fibrinogen Receptor Antagonists Which Present an Alternative Pharmacophere", pp. 9–12.

Ku et al. Journal of American Chemical Society, vol. 115, No. 19, issued Sep. 1993, "Direct Design of a Potent Non–Peptide Fibrinogen Receptor Antagonist Based on the Structure and Conformation of a Highly Constrained Cyclic RGD Reptide", pp. 8861–8862.

* cited by examiner

VITRONECTIN RECEPTOR ANTAGONISTS

This application is a continuation of Ser. No. 09/482,647 filed on Nov. 10, 1998 (aban) which is a continuation of Ser. No. 08/765,753 filed on Dec. 20, 1996 (aban) which is a 371 of PCT/US95/08146 filed on Jun. 29, 1995.

FIELD OF THE INVENTION

This invention relates to pharmaceutically active compounds which inhibit the vitronectin receptor and are useful for the treatment of osteoporosis.

BACKGROUND OF THE INVENTION

Mammalian bone is constantly undergoing bone remodeling, which is a dynamic process of bone resorption and bone formation. These processes are mediated by specialized cell types: bone formation is the result of the deposition of mineralized bone by osteoblast cells, and bone resorption is the result of the dissolution of bone matrix by osteoclast cells. Many bone diseases are brought about by an imbalance of bone formation relative to bone resorption. For instance, diseases such as osteoporosis are characterized by a net loss of bone matrix. Thus, agents which inhibit bone resorption are useful for the treatment of such diseases.

An activated osteoclast resorbs bone by attaching to the bone matrix, and secreting proteolytic enzymes, organic acids and protons into the sealed compartment formed between its cell membrane and the bone matrix. The acidic environment and proteolytic enzymes effect the dissolution of bone in the sealed compartment to create pits, or lacuna, in the bone surface, which are apparent when the osteoclast detaches from the bone.

Recent studies have indicated that the attachment of osteoclasts to the bone matrix is mediated through cell surface adhesion receptors called integrins. For instance, Davies, et al., *J. Cell Biol.*, 1989, 109, 1817, disclose that the osteoclast functional antigen, which is implicated in the regulation of bone resorption, is biochemically related to the vitronectin receptor. The vitronectin receptor, or the $\alpha_v\beta_3$ integrin, is known to bind to bone matrix proteins, such as osteopontin, bone sialoprotein and thrombospondin, which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 disclose that echistatin, a snake venom peptide which contains the RGD sequence, is a potent inhibitor of bone resorption in tissue culture, and inhibits attachment of osteoclasts to bone. Fisher, et al., *Endocrinology* 1993, 132, 1411, has further shown that echistatin inhibits bone resorption in vivo in the rat EP 528 587 and 528 586 report substituted phenyl derivatives which inhibit osteoclast mediated bone resorption.

Bondinell, et al., in WO 93/00095 (PCT/US92/05463) and PCT/US93/12436 disclose that certain compounds which have a substituted 6–7 bicyclic ring system are useful for inhibiting the fibrinogen receptor, which is an integrin ($\alpha_{IIb}\beta_3$) protein founds on platelets. Other 6–7 bicyclic ring systems which inhibit the fibrinogen receptor are disclosed by Blackburn et al. in WO 93/08174 (PCT/US92/08788). It has now been discovered that certain appropriately substituted 1,4-benzodiazepine, -benzothiazepine, -benzoxazepine and 2-benzazepine compounds are potent inhibitors of the vitronectin receptor. In particular, it has been discovered that certain such compounds are suprisingly more potent inhibitors of the vitronectin receptor than the fibrinogen receptor and consequently are more useful in the treatment of diseases such as osteoporosis, cancer, atherosclerosis and for inhibiting restenosis of an artery.

SUMMARY OF THE INVENTION

This invention comprises compounds of the formula (I) as described hereinafter, which have pharmacological activity for the inhibition of the vitronection receptor and are useful in the treatment of osteoporosis.

This invention is also a pharmaceutical composition comprising a compound according to formula (I) and a pharmaceutically carrier.

This invention is also a method of treating diseases which are mediated by ligands which bind to the vitronectin receptor. In a particular aspect, the compounds of this invention are useful for treating osteoporosis, atherosclerosis, restenosis and cancer.

DETAILED DESCRIPTION

This invention comprises compounds of formula (I):

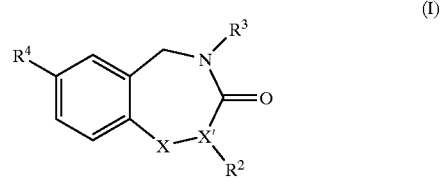

wherein

X—X' is $NR^1$—CH, $NC(O)R^3$—CH, N=C, $CR^1$=C, $CHR^1$—CH, O—CH or S—CH;

$R^1$ is H, $C_{1-6}$ alkyl or benzyl;

$R^2$ is $(CH_2)_nCO_2H$;

$R^3$ is H, $C_{1-6}$alkyl, Ar—$C_{0-6}$alkyl, Het-$C_{0-6}$alkyl, or $C_{3-6}$cycloalkyl-$C_{0-6}$alkyl;

$R^4$ is W—U, Y—$(CHR^5)_m$—U or Z—C(O);

$R^5$ and $R^6$ are independently chosen from H, $C_{1-6}$alkyl, Ar—$C_{0-6}$alkyl, Het-$C_{0-6}$alkyl and $C_{3-6}$cycloalkyl-$C_{0-6}$alkyl;

m is 1 or 2;

n is 1 or 2;

U is $NR^1C(O)$, $C(O)NR^1$, CH=CH, C≡C, $CH_2$—$CH_2$, O—$CH_2$, $CH_2$—O or —$CH_2OCONR^1$;

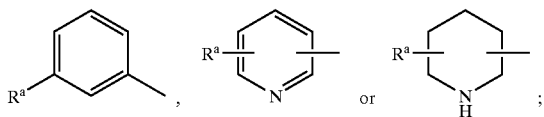

W is $R^a$ is H, OH, $NO_2$, $N(R^6)_2$, $CON(R^6)_2$, $CH_2N(R^6)_2$, or $R^6HN$—C(=NH);

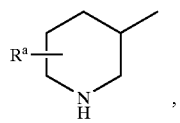

Y is NH$_2$, NHR$^6$, N(R$^6$)$_2$, C(O)N(R$^6$)$_2$, OH, =N—OR$^6$,

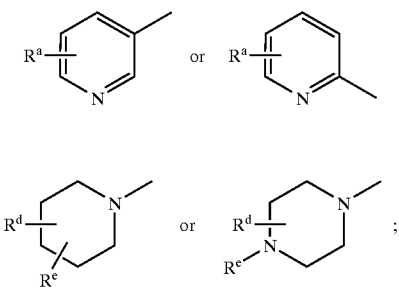

Z is

R$^d$ is H, N(R$^1$), C$_{1-4}$alkyl, CON(R$^1$)$_2$, OH, OR$^1$, or Ar—C$_{0-4}$alkyl;

R$^e$ is H, C$_{1-4}$alkyl, Het-C$_{0-4}$alkyl or Ar—C$_{0-4}$alkyl;

and pharmaceutically acceptable salts thereof, provided that R$^3$ is not phenylethyl when R$^4$ is (3-amidino)phenylaminocarbonyl and X—X' is NH—CH.

The compounds of formula (I) inhibit the binding of vitronectin and other RGD-containing peptides to the vitronectin ($\alpha_v\beta_3$) receptor. Inhibition of the vitronectin receptor on osteoclasts inhibits osteoclastic bone resorption and is useful in the treatment of diseases wherein bone resorption is associated with pathology, such as osteoporosis.

Suitably, X—X' is NH—CH or CH$_2$—CH.

Preferably, U is NR$^1$CO, CONR$^1$ or CH$_2$OCONR$^1$. More preferably U is NR$^1$CO.

Suitably R$^a$ is hydroxy or amino. Preferably R$^a$ is amino.
Suitably W is

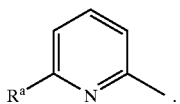

Preferably, W is

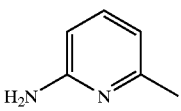

or (3-amidino)phenyl.
Suitably Y is

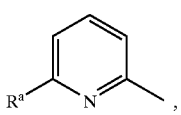

OH or NHR$^6$. Suitably R$^5$ is H, phenyl or C$_{1-6}$alkyl. Suitably R$^6$ is benzyl, 2-pyridinyl or H.

Suitably Z is 1-piperazinyl or 1-piperidinyl.

Suitably R$^4$ is Y—(CH$_2$)$_m$NCH$_3$CO.

Suitably R$^e$ is H or substituted or unsubstituted phenyl, benzyl, 2- or 3-pyridinyl, 2- or 4-pyrimidinyl or 1-, 2- or 3-piperidinyl. When Z is 1-piperazinyl, R$^e$ is preferably 2- or 3-pyridinyl or 2- or 4-pyrimidinyl. When Z is piperidinyl, R$^e$ is preferably 1-piperidinyl.

Preferably Y is NH$_2$ or pyridinyl.
Preferably n is 1.
Preferably R$^1$ is H, methyl or phenylethyl.
Representative of the novel compounds of this invention are the following:

(±)-7-[[(6-Amino-2-pyridinyl)amino]carbonyl]-4-methyl-3-oxo-2,3,4,5-tetrahydro-1H-1,4-benzodiazepine-2-acetic acid;

(±)-8-[[(6-amino-2-pyridinyl)amino]carbonyl]-2-methyl-3-oxo-2,3,4,5-tetrahydro1H-2-benzazepine-4-acetic acid;

(±)-7-[[(6-amino-3-pyridinyl)amino]carbonyl]-3-oxo-4-(2-phenylethyl)-2,3,4,5-tetrahydro-1H-1,4-benzodiazepine-2-acetic acid;

(±)-1-Acetyl-7-[[(6-amino-2-pyridinyl)amino]carbonyl]-4-methyl-3-oxo-2,3,4,5-tetrahydro-1H-1,4-benzodiazepine-2-acetic acid;

(±)-2-methyl-3-oxo-8-[[2-(pyridinyl)carbonyl]amino]-2,3,4,5-tetrahydro-1H-2-benzazepine-4-acetic acid;

(±)-8-[(benzyloxycarbonyl)amino]-2-methyl-3-oxo-2,3,4,5-tetrahydro-1H-2-benzazepine-4-acetic acid;

(±)-7-[[[3-(aminoiminomethyl)phenyl]amino]carbonyl]-4-methyl-3-oxo-2,3,4,5-tetrahydro-1H-1,4-benzodiazepine-2-acetic acid;

(±)-7-[[[3-(aminocarbonyl)phenyl]amino]carbonyl]-4-methyl-3-oxo-2,3,4,5-tetrahydro-1H-1,4-benzodiazepine-2-acetic acid;

(±)-4-methyl-3-oxo-7-[1-(4-phenylpiperazinyl)carbonyl]-2,3,4,5-tetrahydro-1H-1,4-benzodiazepine-2-acetic acid;

(±)-4-methyl-3-oxo-7-[(1-piperazinyl)carbonyl]-2,3,4,5-tetrahydro-1H-1,4-benzodiazepine-2-acetic acid;

(±)-4-methyl-3-oxo-7-[1-[4-(1-piperidinyl)piperidinyl]carbonyl]-2,3,4,5-tetrahydro-1H-1,4-benzodiazepine-2-acetic acid;

(±)-4-methyl-3-oxo-7-[1-[4-(2-pyridinyl)piperazinyl]carbonyl]-2,3,4,5-tetrahydro-1H-1,4-benzodiazepine-2-acetic acid;

(±)-4-methyl-3-oxo-7-[1-[4-(phenylmethyl)piperazinyl]carbonyl]-2,3,4,5-tetrahydro-1H-1,4-benzodiazepine-2-acetic acid;

(±)-4-methyl-3-oxo-7-[1-[4-(2-pyrimidinyl)piperazinyl]carbonyl]-2,3,4,5-tetrahydro-1H-1,4-benzodiazepine-2-acetic acid;

8-[[2S-amino-3-phenylpropanoyl]amino]-2-methyl-3-oxo-2,3,4,5-tetrahydro-1H-2-benzazepine-4RS-acetic acid;

(±)-8-[[[(2-hydroxy-2-phenyl)ethyl]methylamino]carbonyl]-2-methyl-3-oxo-2,3,4,5-tetrahydro-1H-2-benzazepine-4-acetic acid;

(±)-7-[[[N-(2-hydroxyethyl)-N-methyl]amino]carbonyl]-4-methyl-3-oxo-2,3,4,5-tetrahydro-1H-1,4-benzodiazepine-2-acetic acid;

(±)-8-[[(2-(2-pyridinylamino)acetyl]amino]-2-methyl-3-oxo-2,3,4,5-tetrahydro-1H-2-benzazepine-4-acetic acid;

(±)-4-methyl-3-oxo-7-[[(2-phenylaminoethyl)amino]carbonyl]-2,3,4,5-tetrahydro-1H-1,4-benzodiazepine-2-acetic acid;

(±)-8-[(2-aminoacetyl)amino]-2-methyl-3-oxo-2,3,4,5-tetrahydro-1h-2-benzazepine-4-acetic acid;

(+/-)-8-[(3-aminopropanoyl)amino]-2-methyl-3-oxo-2,3,4,5-tetrahydro-1H-2-benzazepine-4-acetic acid; and (±)-4-methyl-3-oxo-7-[[[(3-pyridinyl)methyl]amino]carbonyl]-2,3,4,5-tetrahydro-1H-1,4-benzodiazepine-2-acetic acid;

Other compounds useful in the method of inhibiting the vitronectin receptor are:

(±)-7-[[[3-(Aminoiminomethyl)phenyl]amino]carbonyl]-3-oxo-4-(2-phenylethyl)-2,3,4,5-tetrahydro-1H-1,4-benzodiazepine-2-acetic acid.

(±)-7-[1-[4-(2-Methyl-4-pyridinyl)piperazinyl]carbonyl]-4-methyl-3-oxo-2,3,4,5-tetrahydro-1H-1,4-benzodiazepine-2-acetic acid;

(±)-3-Oxo-4-(2-phenylethyl)-7-[1-[4-(4-pyridinyl)piperazinyl]carbonyl]-2,3,4,5-tetrahydro-1H-1,4-benzodiazepine-2-acetic acid; and (±)-4-Methyl-3-oxo-7-[1-[4-(4-pyridinyl)piperazinyl]carbonyl]-2,3,4,5-tetrahydro-1H-1,4-benzodiazepine-2-acetic acid.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochen,* 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicate that no alkyl group need be present (e.g., that a covalent bond is present).

A substituent on a $C_{1-6}$ alkyl group, may be on any carbon atom which results in a stable structure, and is available by conventional synthetic techniques. Suitable substituents are $C_{1-4}$alkyl, $OR^1$, $SR^1$, $C_{1-4}$alkyl, $C_{1-4}$alkylsulfonyl, $C_{1-4}$alkylsulfoxyl, —CN, $N(R^1)_2$, $CH_2N(R^1)_2$, —$NO_2$, —$CF_3$, —$CO_2R^{'3}$, —$CON(R^1)_2$, —$COR^1$, —$NR^1C(O)R^1$, OH, F, Cl, Br, I, or $CF_3S(O)_r$—, wherein r is 0 to 2.

Ar, or aryl, as applied herein, means phenyl or naphthyl, or phenyl or naphthyl substituted by one to three substituents, such as those defined above for alkyl, especially $C_{1-4}$alkyl, $C_{1-4}$alkoxy, $C_{1-4}$alkthio, trifluoroalkyl, OH, F, Cl, Br, I or a 1,2-methylene dioxy group.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro- quinoline and isoquinoline. Any accessible combination of up to three substituents on the Het ring, such as those defined above for alkyl that are available by chemical synthesis and are stable are within the scope of this invention.

$C_{3-7}$cycloalkyl refers to an optionally substituted carbocyclic system of three to seven carbon atoms, which may contain up to two unsaturated carboncarbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, CIZ refers to the o-chlorobenzyloxycarbonyl radical, Bn refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. MeArg is $N^\alpha$-methyl arginine. Tet refers to 5-tetrazolyl.

Certain reagents are abbreviated herein. DCC refers to dicyclohexylcarbodiimide, DMAP refers to dimethylaminopyridine, DIEA refers to diisopropylethylamine, EDC refers to N-ethyl-N'(dimethylaminopropyl)-carbodiimide. HOBt refers to 1-hydroxybenzotriazole, THF refers to tetrahydrofuran, DMF refers to dimethyl formamide, NBS refers to N-bromo-succinimide, Pd/C refers to a palladium on carbon catalyst, DPPA refers to diphenylphosphoryl azide, BOP refers to benzotriazol-1-yloxy-tris(dimethylamino) phosphonium hexafluorophosphate, HF refers to hydrofluoric acid, TEA refers to triethylamine, TFA refers to trifluoroacetic acid, PCC refers to pyridinium chlorochromate.

Compounds of the formula (I) are prepared by the general methods described in Schemes I–III.

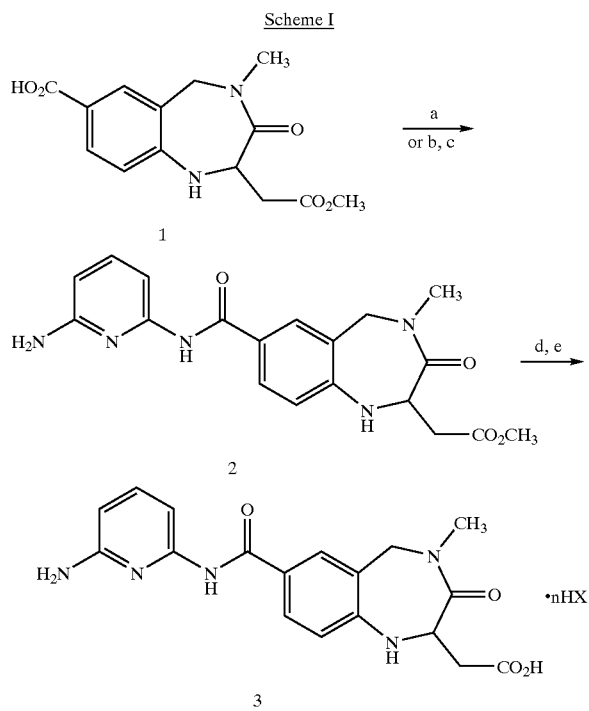

Scheme I a) EDC, HOBT, (i-Pr)$_2$NEt, DMF, 2-aminopyridine;
b) SOCl$_2$, reflux;
c) 2-2aminopyridine, pyridine, CH$_2$Cl;
d) 1.0 N LiOH, aqueous THF;
e) acidification.

Methyl (±)-7-carboxy-4-methyl-3-oxo-2,3,4,5-tetrahydro-1H-1,4-benzodiazepine-2-acetate (I-1), prepared as described by Bondinell, et al. (WO 93/00095), is converted to an activated form of the carboxylic acid using, for example, EDC and HOBT or SOCl$_2$, and the activated form is subsequently reacted with an appropriate amine to afford the corresponding amide I-2. Many additional methods for converting a carboxylic acid to an amide are known, and can be found in standard reference books, such as "Compendium of Organic Synthetic Methods", Vol. I–VI (published by Wiley-Interscience). The methyl ester of I-2 is hydrolyzed using aqueous base, for example, aqueous LiOH in THF or aqueous NaOH in methanol, and the intermediate carboxylate salt is acidified with a suitable acid, for instance TFA or HCl, to afford the carboxylic acid I-3. Alternatively, the intermediate carboxylate salt can be isolated, if desired.

Scheme II

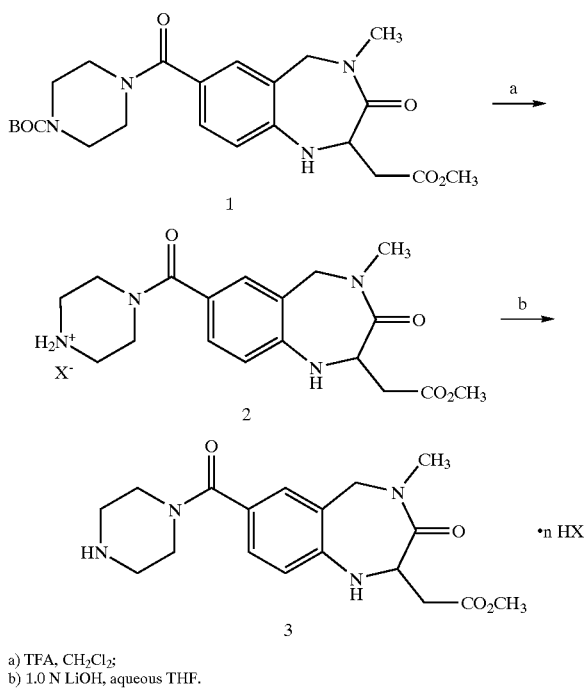

a) TFA, CH$_2$Cl$_2$;
b) 1.0 N LiOH, aqueous THF.

If the amine partner contains a protecting group, the protecting group can be removed either prior or subsequently to the ester hydrolysis step, using methods suitable for selective deprotection of the specific protecting group employed. Such methods are described in Green, "Protective Groups in Organic Synthesis" (published by Wiley-Interscience). For example, if the amine partner contains a nitrogen group which is protected by a tert-butoxycarbonyl (BOC) group, such as in compound II-1 (prepared by the general methods described above), the BOC group is removed using acidic conditions, such as TFA in CH$_2$Cl$_2$ or HCl in dioxane, to afford the intermediate ammonium salt II-2. Subsequent ester hydrolysis followed by acidification is accomplished as described in Scheme I to afford II-3.

Scheme III

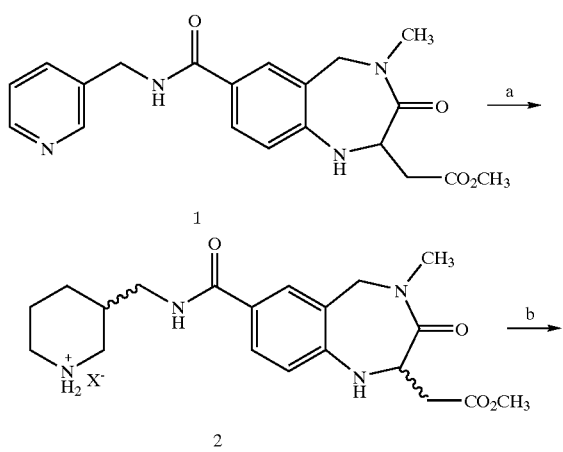

-continued

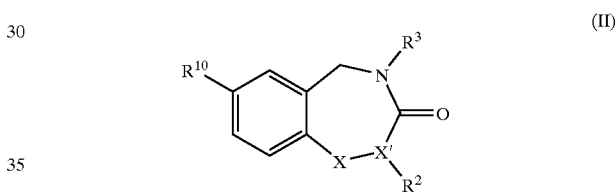

a) H$_2$, PtO$_2$, 1.0 N HCl, MeOH;
b) 1.0 N LiOH, aqueous THF

Piperidine-containing compounds, such as III-3, can be prepared either from a suitably N-protected piperidine derivative, according to the methods described in Schemes I and II, or from a pyridine precursor, such as III-1. For example, the pyridine subunit of III-1 can be reduced to the corresponding piperidine group by hydrogenation over a suitable catalyst, preferably PtO$_2$, in the presence of acid, such as HCl. The resulting piperidinium salt III-2 is then converted to compound III-3 by the methods described in Scheme I.

The core 6–7 fused ring system is prepared from compounds of the general formula (II):

(II)

$$\text{R}^{10}\text{—}\underset{\underset{R^2}{X-X'}}{\overset{\overset{R^3}{N}}{\bigcirc}}=O$$

wherein $R^{10}$ is NHR$^1$, CO$_2$H and synthetic equivalents thereof, X and X' are as defined for formula (I) and $R^2$ and $R^3$ are as defined in formula (I) with any reactive groups protected. Representative methods for preparing the substituted benzodiazepine nucleus are well known in the art, e.g., Hynes, et al., *J. Het. Chem.*, 1988, 25, 1173; Muller, et al., *Helv. Chim. Acta.*, 1982, 65, 2118; Mori, et al., *Heterocycles*, 1981, 16, 1491. Similarly, methods for preparing benzazepines, 1,4-benzothiazepines, 1,4-benzoxazepines and 1,4-benzodiazepines are known and are disclosed, for instance, in Bondinell, et al., International Patent Application WO 93/00095.

Representative methods for preparing the benzodiazepine nucleus are given by Schemes IV–VI. A representative method for preparing a benzazepine nucleus is given by Scheme VII. A representative method for preparing a benzothiazepine is given by Scheme VIII. An benzoxazepine nucleus may be prepared in the same manner as Scheme VIII, except substituting a benzyl alcohol for a benzyl thiol.

Scheme IV

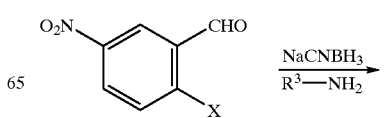

Scheme VI
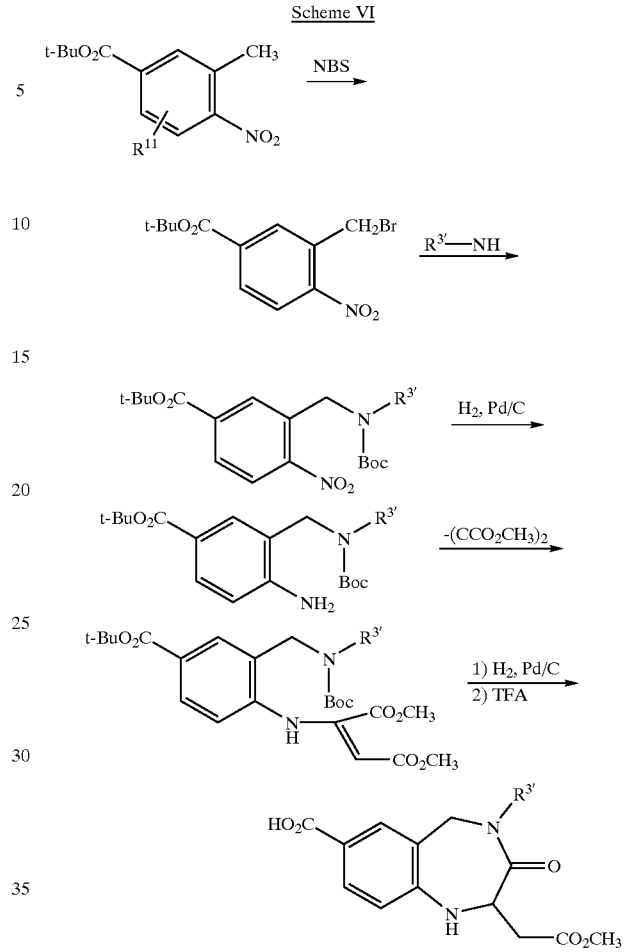
Scheme V
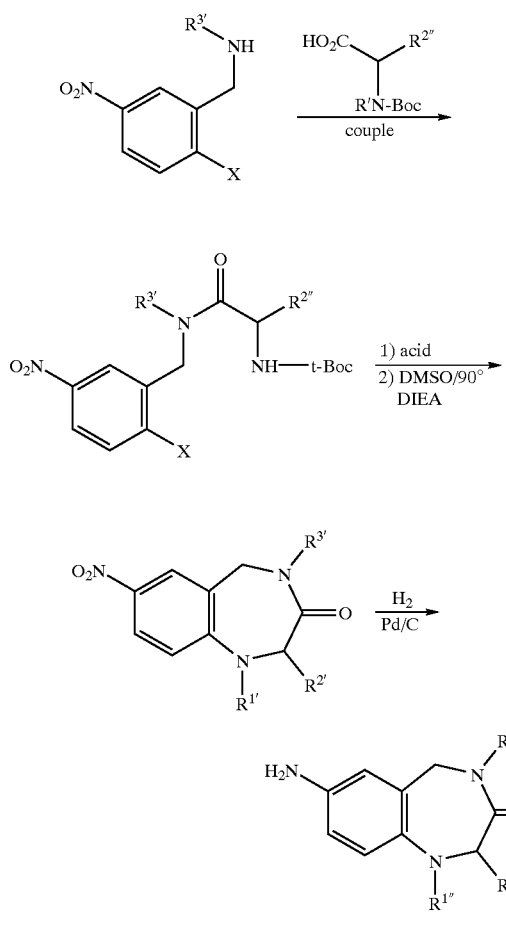
Scheme VII
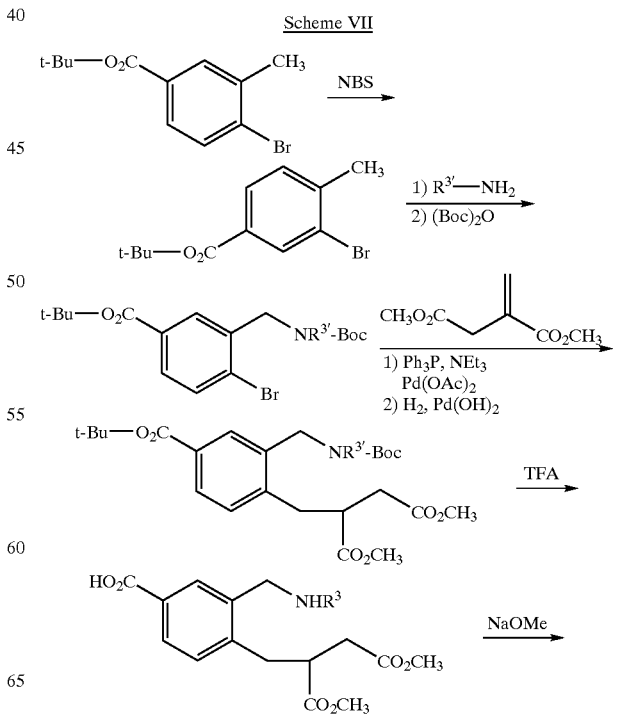
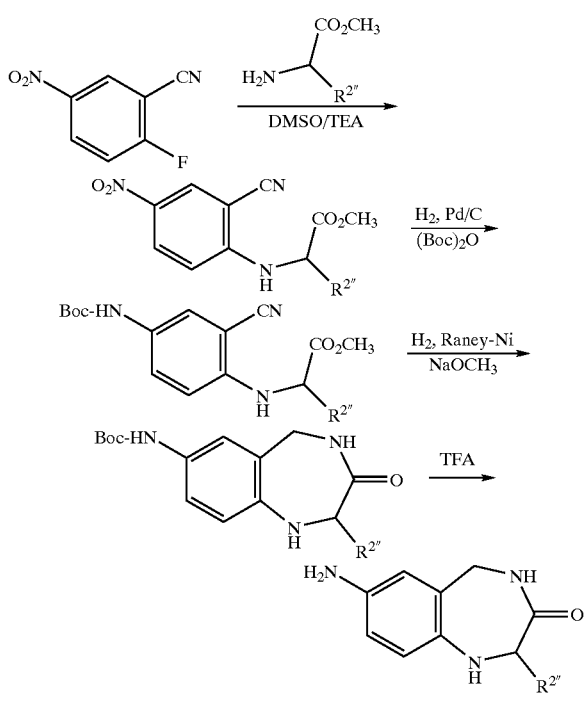

-continued

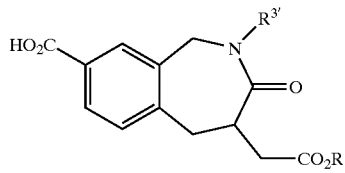

NBS = N-bromosuccinimide

Scheme VIII

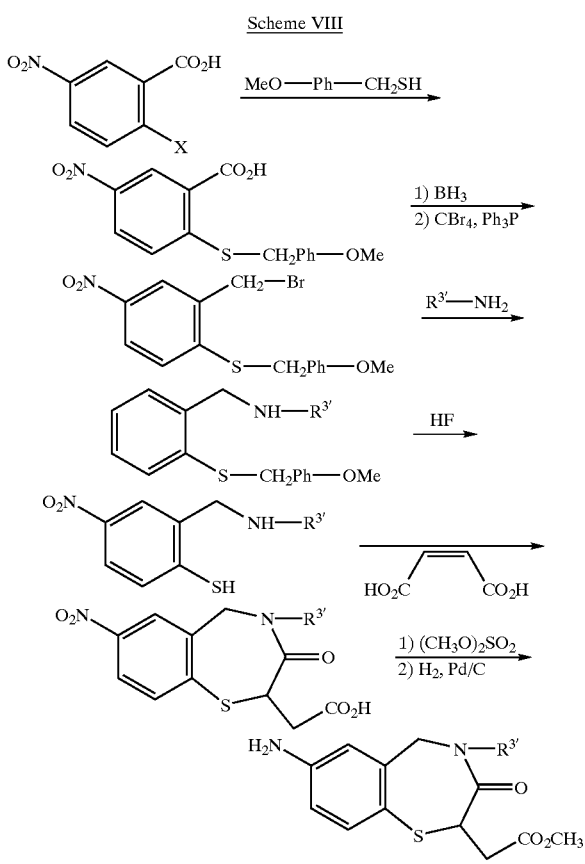

The simple tri-substituted benzene starting materials are commercially available or prepared by routine methods well known in the art.

Coupling reagents as used herein denote reagents which may be used to form peptide bonds. Typical coupling methods employ carbodiimides, activated anhydrides and esters and acyl halides. Reagents such as EDC, DCC, DPPA, BOP reagent, HOBt, N-hydroxysuccinimide and oxalyl chloride are typical.

Coupling methods to form peptide bonds are generally well known to the art. The methods of peptide synthesis generally set forth by Bodansky et al., The Practice of Peptide Synthesis, Springer-Verlag, Berlin, 1984, Ali et al. in J. Med. Chem., 29, 984 (1986) and J. Med. Chem., 30, 2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch. lactose, calcium sulfate dihydrate, terra alba, magnesium stearate or stearic acid, talc, pectin, acacia. agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, antiinflammatory, anti-angiogenic and anti-metastatic agents, and be useful in the treatment of cancer, atherosclerosis and restenosis.

The peptide is administered either orally or parenterally to the patient, in a manner such that the concentration of drug is sufficient to inhibit bone resorption, or other such indication. The pharmaceutical composition containing the peptide is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

The compounds may be tested in one of several biological assays to determine the concentration of compound which is required to have a given pharmacological effect.

Inhibition of Vitronectin Binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 μg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 μM. This solution is then diluted to the required final compound concentration. Various concentrations of unlabeled antagonists (0.001–100 μM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 μM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to the equation: $K_i=IC_{50}/(1+L/K_d)$, where L and $K_d$ were the concentration and the dissociation constant of [$^3$H]-SK&F-$107260$, respectively.

Compounds of the present invention inhibit vitronectin binding to SK&F 107260 in the concentration range of 0.1 to 25 micromolar. Preferred compounds inhibit vitronectin binding at a concentration of less than 1 micromolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Parathyroidectomized Rat Model

Each experimental group consists of 5–6 male Sprague-Dawley rats. The rats are parathyroidectomized (by the vendor, Taconic Farms) 7 days prior to use. Twenty four hours prior to use, circulating ionized calcium levels are measured in whole blood immediately after it has been withdrawn by tail venipuncture into heparinized tubes. Rats are included if ionized Ca level (measured with a Ciba-Corning model 634 calcium pH analyzer) is ≦1.2 mM/L. The rats are then put on a diet of calcium-free chow and deionized water. At the start of the experiment the rats weigh approximately 100 g. Baseline Ca levels are measured and the rats are administered control vehicle (saline) or compound (dissolved in saline) as a single intravenous (tail vein) bolus injection followed immediately by a single subcutaneous injection of either human parathyroid hormone 1-34 peptide (hPTH1-34, dose 0.2 mg/kg in saline/0.1% bovine serum albumen, Bachem, Calif.) or the PTH vehicle. The calcemic response to PTH (and any effect of compound on this response) is measured 2 h after compound/PTH administration.

Rat Ulna Drift Model

Each experimental group consists of 8–10 male Sprague-Dawley or Wistar rats of approximately 30–40 g body weight at the start of the experiment. The agent being tested is administered by an appropriate route as single or multiple daily doses for a period of seven days. Prior to administration of the first dose, the rats are given a single dose of a fluorescent marker (tetracycline 25 mg/kg, or calcein 10 mg/kg) that labels the position of bone forming surfaces at that point in time. After dosing of compound has been completed, the rats are killed and both forelimbs are removed at the elbow, the foot is removed at the ankle and the skin removed. The sample is frozen and mounted vertically on a microtome chuck. Cross sections of the midshaft region of the ulna are cut in the cryostat. The rate of bone resorption is measured morphometrically in the medial-dorsal portion of the cortical bone. The measurement is done as follows: the amount of bone resorbed at the periosteal surface is equal to the distance by which the periosteal surface has advanced towards the fluorescent label which had been incorporated at the endosteal bone formation surface on day zero; this distance is calculated by subtracting the width of bone between the label and the periosteal surface on day 7 from the width on day zero; the resorption rate in microns per day is calculated by dividing the result by 7.

Human Osteoclast Resorption Assay ("Pit Assay")

Aliquots of osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

Aspirate the medium and replace it with murine anti-HLA-DR antibody, diluted 1:3 in RPMI-1640 medium. Incubate for 30 mins on ice and mix the cell suspension frequently.

The cells are washed ×2 with cold RPMI-1640 by centrifugation (1000 rpm, 5 mins at 4° C.) and the cells are transferred to a sterile 15 ml centrifuge tube. The number of mononuclear cells are enumerated in an improved Neubauer counting chamber.

Sufficient magnetic beads (5/mononuclear cell), coated with goat anti-mouse IgG, are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The osteoclasts are enumerated in a counting chamber, using a large-bore disposable plastic pasteur to charge the chamber with the sample.

The cells are pelleted by centrifugation and the density of osteoclasts adjusted to $1.5 \times 10^4$/ml in EMEM medium, supplemented with 10% fetal calf serum and 1.7 g/liter of sodium bicarbonate.

3 ml aliquots of the cell suspension (per treatment) are decanted into 15 ml centrifuge tubes. The cells are pelleted by centrifugation.

To each tube 3 ml of the appropriate treatment are added (diluted to 50 uM in the EMEM medium). Also included are appropriate vehicle controls, a positive control (87MEM1 diluted to 100 ug/ml) and an isotype control (IgG2a diluted to 100 ug/ml). Incubate at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh treatment or control. Incubate at 37° C. for 48 hours. tartrate resistant acid phosphatase (trap) procedure (selective stain for cells of the osteoclast lineage).

The slices are washed in phosphate buffered saline and fixed in 2% gluteraldehyde (in 0.2M sodium cacodylate) for 5 mins.

They are washed in water and incubated in TRAP buffer for 5 mins at 37° C.

Following a wash in cold water they are incubated in cold acetate buffer/fast red garnet for 5 mins at 4° C.

Excess buffer is aspirated, and the slices are air dried following a wash in water.

The TRAP positive osteoclasts are enumerated by brightfield microscopy and are then removed from the surface of the dentine by sonication.

Pit volumes are determined using the Nikon/Lasertec ILM21W confocal microscope.

Inhibition of RGD-Mediated GPIIB-IIIA Binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM $CaCl_2$ (with 2 changes). The GPIIb-IIIa-containing liposomes were centrifuged at 12,000 g for 15 min and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly. (Millipore Corporation, Bedford, Mass.) using 0.22 um hydrophilic durapore membranes. The wells were precoated with 0.2 mL of 10 $\mu$g/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 $\mu$g of the purified platelet GPIIb-IIIa-containing liposomes. The mixtures were incubated for 1 h at room temperature. The GPIIb-IIIa-bound [$^3$H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 $\mu$M unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis.

Preferred compounds of this invention have an affinity for the vitronectin receptor relative to the fibrinogen receptor of greater than 3:1. More preferred compounds have a ratio of activity of greater than 10:1. The comparative results of enhanced binding of the compounds of this invention to the vitronecton receptor relative to the fibrinogen receptor are given in Table 1 below:

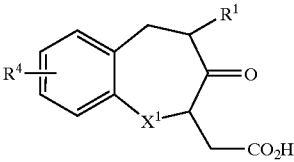

| | R⁴ = W-U | | | | | |
|---|---|---|---|---|---|---|
| Ex | X¹ | U | W | $\alpha_V\beta_3(\mu M)$ | $\alpha_{IIb}\beta_3(\mu M)$ | ratio* |
| 1 | NH | NHCO | 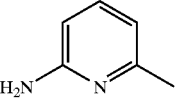 | 0.15 | 160 | 1067 |
| 2 | CH₂ | NHCO | 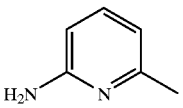 | 0.65 | >50 | 77 |
| 3 | NH | NHCO | 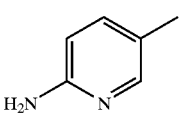 | 9.18 | 110 | 12 |
| 4 | NAc | NHCO | 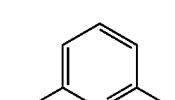 | 15.1 | >100 | >7 |
| 5 | CH₂ | CONH | 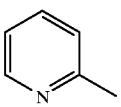 | 15.3 | >50 | >3 |
| 6 | CH₂ | CH₂OCONH | 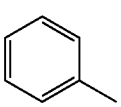 | 7.50 | 17.5 | 2.3 |
| 7 | NH | NHCO | 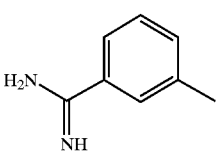 | 1.50 | 5.05 | 3.4 |
| 8 | NH | NHCO | 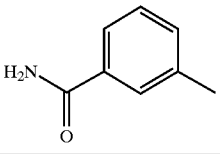 | 12.3 | >50 | >4 |
| | R⁴ = Z-CO | | | | | |
| Ex | X¹ | Z | | $\alpha_V\beta_3(\mu M)$ | $\alpha_{IIb}\beta_3(\mu M)$ | ratio* |
| 9 | NH | CO | 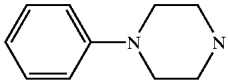 | 9.23 | >100 | >11 |

-continued

[Structure: benzazepine core with R¹, R⁴, X¹, and CH₂-CO₂H substituents]

| Ex | X¹ | | | $\alpha_V\beta_3$ (μM) | $\alpha_{IIb}\beta_3$ (μM) | ratio* |
|---|---|---|---|---|---|---|
| 10 | NH | CO | piperazine (HN-N) | 1.10 | 2.13 | >1.9 |
| 11 | NH | CO | 4-piperidinyl-piperidine | 1.45 | 20.1 | 14 |
| 12 | NH | CO | 2-pyridyl-piperazine | 1.25 | 40.5 | 32 |
| 13 | NH | CO | benzyl-piperazine | 9.5 | 15.4 | 1.62 |
| 14 | NH | CO | 2-pyrimidinyl-piperazine | 6.2 | >50 | >8 |

| | $R^4 = Y\text{-}(CHR)_mU$ | | | | | |
|---|---|---|---|---|---|---|
| Ex | X¹ | —(CHR)m-U | Y | $\alpha_V\beta_3$ (μM) | $\alpha_{IIb}\beta_3$ (μM) | ratio* |
| 15 | CH₂ | CHPhCONH | NH₂ | 3.90 | 37.5 | 9.6 |
| 16 | CH₂ | CHPhCONMe | OH | 9.50 | 28.0 | 2.9 |
| 17 | NH | NMeCO | HO-CH₂CH₂-NCH₃ | 15.2 | >50 | >3 |
| 18 | CH₂ | CH₂CONH | 2-pyridyl-NH-methyl | 1.3 | 30.0 | 23 |
| 19 | NH | CH₂CH₂NHCO | NHPh | 22.0 | >50 | >2.3 |
| 20 | CH₂ | CH₂CONH | NH₂ | 1.55 | 45.0 | 29 |
| 21 | CH₂ | CH₂CH₂CONH | NH₂ | 0.85 | 52.0 | 61 |
| 22 | NH | CH₂NHCO | 3-methylpyridyl | 9.02 | 27.0 | 3 |

*enhanced binding to vitronectn receptor vs fibrinogen receptor = $\alpha_{IIb}\beta_3/\alpha_V\beta_3$ Vascular Smooth Muscle Cell Migration Assay The compounds of the instant invention were tested for their ability to inhibit the migration and proliferation of smooth muscle tissue in an artery or vein in order to assess their ability to prevent restenosis of an artery, such as that which typically occurs following angioplasty.

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of 2.5–5.0×10⁶ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% CO₂ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

EXAMPLES

Nuclear magnetic resonance spectra were recorded at either 250 or 400 MHz using, respectively, a Bruker AM 250 or Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Infrared (IR) spectra were recorded on a Perkin-Elmer 683 infrared spectrometer in transmission mode. IR band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240 C. elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support 5µ Apex-ODS indicates an octadecylsilyl derivatized silica gel chromatographic support having a nominal particle size of 5 g, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Methyl (±)-7-carboxy-3-oxo-2-(2-phenylethyl)-2,3,4,5-tetrahydro-1H-1,4-benzodiazepine-2-acetate, methyl (±)-7-carboxy-4-methyl-3-oxo-2,3,4,5-tetrahydro-1H-1,4-benzodiazepine-2-acetate, and 3-amino-(N-benzyloxycarbonyl)benzamidine were prepared by the method of Bondinell, et al., WO 93/00095. Methyl (±)-8-carboxy-2-methyl-3-oxo-2,3,4,5-tetrahaydro-1H-2-benzazepine-4-acetate was prepared by the method disclosed in Example 1 of WO 94/14776, except substituting 4-bromo-3-methylbenzoic acid for 3-bromo-4-methylbenzoic acid and substituting methylamine for phenethylamine therein. 4-(2-Methylpyridyl)piperazine was prepared by the procedure of Cross and Dickinson, U.S. Pat. No. 4,806,536 (Feb. 21, 1989).

Example 1

Preparation of (±)-7-[[(6-Amino-2-pyridinyl)amino]carbonyl]-4-methyl-3-oxo-2,3,4,5-tetrahydro-1H-1,4-benzodiazepine-2-acetic acid a) Methyl (±)-7-[[(6-amino-2-pyridinyl)amino]carbonyl]-4-methyl-3-oxo-2,3,4,5-tetrahydro-1H-1,4-benzodiazepine-2-acetate Diisopropylethylamine (0.29 g, 2.25 mmol) was added in one portion to a stirred mixture of 2,6-diaminopyridine (0.2 g, 1.8 mmol), methyl (±)-7-carboxy-4-methyl-3-oxo-2,3,4,5-tetrahydro-1H-1,4-benzodiazepine-2-acetate (0.44 g, 1.50 mmol), EDC (0.34 g, 1.8 mmol) and $HOBT.H_2O$ (0.24 g, 1.8 mmol) in DMF (8 mL) at RT under argon. After 24 h, the brownish solution was poured into a mixture of ice-water (90 g) and 5% $NaHCO_3$ (10 mL). The resulting precipitate was filtered and air-dried to give an off-white solid (0.53 g). Flash chromatography (silica gel, 7% $MeOH/CH_2C_2$) yielded the title compound (0.04 g, 7%): $^1H$ NMR (250 MHz, $CDCl_3$) δ6.26–8.20 (m, 6H), 5.47 (d, J=16 Hz, 1H), 5.12 (dd, J=11, 6 Hz, 1H), 4.59 (d, J=4 Hz, 2H), 3.80 (d, J=16 Hz, 1H), 3.76 (s, 3H), 3.09 (s, 3H), 3.00 (dd, J=16, 6 Hz, 1H), 2.68 (dd, J=16, 6 Hz, 1H); MS (ES) m/e 384.2 $(M+H)^+$.

b) (±)-7-[[(6-Amino-2-pyridinyl)amino]carbonyl]-4-methyl-3-oxo-2,3,4,5-tetrahydro-1H-1,4-benzodiazepine-2-acetic acid 1.0 N LiOH (0.26 mL, 0.26 mmol) was added dropwise in RT to a mixture of methyl (±)-7-[[(6-amino-2-pyridinyl)amino]carbonyl]-4-methyl-3-oxo-2,3,4,5-tetrahydro-1H-1,4-benzodiazepine-2-acetate (0.044 g, 0.12 mmol) in THF (4 mL) and $H_2O$ (5 mL). The resulting light yellowish-brown solution was stirred for 23 h, then was concentrated on the rotavap. The resulting residue was lyophilized to give the crude product as a yellowish powder (0.051 g). Preparative HPLC (PRP-1® column, step gradient, 10–15% $CH_3CN$/$H_2O$-0.1% TFA) afforded the title compound: $^1H$ NMR (250 MHz, $DMSO-d_6$) δ10.75 (br, 1H), 6.46–8.29 (m, 6H), 5.73 (s, 1H), 5.53 (d, J=17 Hz, 1H), 5.17 (br, 1H), 3.88 (d, J=17 Hz, 1H), 2.96 (s, 3H), 2.83 (dd, J=17, 9 Hz, 1H), 2.58 (dd, J=17, 5 Hz, 1H); MS (ES) m/e 370.2 $(M+H)^+$. Anal. Calcd for $C_{18}H_{19}N_5O_4.9/4CF_3CO_2H.1/2H_2O$: C, 42.56; H, 3.53; N, 11.03. Found: C, 42.20; H, 3.02; N, 11.36.

Example 2

Preparation of (±)-8-[[(6-amino-2-pyridinyl)amino]carbonyl]-2-methyl-3-oxo-2,3,4,5-tetrahydro-1H-2-benzazepine-4-acetic acid a) Methyl (±)-8-[[(6-amino-2-pyridinyl)amino]carbonyl]-2-methyl-3-oxo-2,3,4,5-tetrahydro-1H-2-benzazepine-4-acetate A mixture of methyl (±)-8-carboxy-2-methyl-3-oxo-2,3,4,5-tetrahaydro-1H-2-benzazepine-4-acetate (300 mg, 1.03 mmol) and thionyl chloride (10 mL) was refluxed for 1 h. The resulting solution was concentrated to dryness to yield a foam. This was dissolved in $CH_2Cl_2$ (10 mL) and added dropwise to a solution of 2,6-diaminopyridine (0.34 g, 3.09 mmol) in $CH_2Cl_2$ (10 mL) and DMF (3 mL) at RT under argon. After 110 min, the reaction mixture was partitioned between $CH_2Cl_2$ (150 mL) and 5% $NaHCO_3$ (70 mL). The organic layer was separated, washed sequentially with 5% $NaHCO_3$ (50 mL) and $H_2O$ (50 mL), dried ($Na_2SO_4$), and concentrated to leave a yellowish solid (0.69 g). Recrystallization from $MeOH/CH_2Cl_2/EtOAc$ afforded the title compound (0.16 g, 41%): $^1H$ NMR (250 MHz, $CDCl_3/DMSO-d_6$) δ6.63–10.00 (m, 6H), 5.71 (s, 2H), 5.30 (d, J=16 Hz, 1H), 4.07 (d, J=17 Hz, 1H), 3.83 (m, 1H), 3.61 (s, 3H), 2.93 (s, 3H), 2.71–3.25 (m, 3H), 2.45 (dd, J=17, 5 Hz, 1H); MS (ES) m/e 383.2 $(M+H)^+$.

b) (±)8-[[(6-Amino-2-pyridinyl)amino]carbonyl]-2-methyl-3-oxo-2,3,4,5-tetrahydro-1H-2-benzazepine-4-acetic acid 1.0 N LiOH (0.92 mL, 0.92 mmol) was added dropwise at RT to a mixture of the compound of Example 2(a) (160 mg, 0.42 mmol) in THF (6.5 mL) and H$_2$O (8 mL). The resulting solution was stirred for 21.5 h, then concentrated on the rotavap. The resulting residue was lyophilized to give the crude product, and purified by preparative HPLC (PRP-1® column, step gradient, 10–20% CH$_3$CN/H$_2$O-0.1% TFA) to yield the title compound: $^1$H NMR (250 MHz, DMSO-d$_6$) δ11.13 (br, 1H), 6.52–7.88 (m, 6H), 5.35 (d, J=16 Hz, 1H), 4.10 (d, J=17 Hz, 1H), 3.82 (m, 1H), 2.94 (s, 3H), 2.53–3.22 (m, 3H), 2.37 (dd, J=17, 5 Hz, 1H); MS (ES) m/e 369.2 (M+H)$^+$. Anal. Calcd for C$_{19}$H$_{20}$N$_4$O$_4$.3/2CF$_3$CO$_2$H: C, 48.99; H, 4.02; N, 10.39. Found: C, 48.75; H, 4.23; N, 10.35.

Example 3

Preparation of (±)-7-[[(6-amino-3-pyridinyl)amino] carbonyl]-3-oxo-4-(2-phenylethyl)-2,3,4,5-tetrahydro-1H-1,4-benzodiazepine-2-acetic acid a) Methyl (±)-7-[[(6-amino-3-pyridinyl)amino] carbonyl]-3-oxo-4-(2-phenylethyl)-2,3,4,5-tetrahydro-1H-1,4-benzodiazepine-2-acetate Following the procedure of Example 1(a), substituting methyl (±)-7-carboxy-3-oxo-2-(2-phenylethyl)-2,3,4,5-tetrahydro-1H-1,4-benzodiazepine-2-acetate for methyl (±)-7-carboxy-4-methyl-3-oxo-2,3,4,5-tetrahydro-1H-1,4-benzodiazepine-2-acetate, and substituting 2,5-diaminopyridine for 2,6-diaminopyridine, the title compound was prepared (0.42 g, 42%): $^1$H NMR (250 MHz, CDCl$_3$/DMSO-d$_6$) δ6.14–9.46 (m, 7H), 5.35–5.44 (br, 3H), 5.13 (m, 1H), 3.68 (s, 3H), 3.55–3.83 (m, 3H), 2.94 (dd, J=17, 8 Hz, 1H), 2.78 (t, 2H), 2.66 (dd, J=17, 5 Hz, 1H); MS (ES) m/e 474.2 (M+H)$^+$.

b) (±)-7-[[(6-Amino-3-pyridinyl)amino]carbonyl]-3-oxo-4-(2-phenylethyl)-2,3,4,5-tetrahydro-1H-1,4-benzodiazepine-2-acetic acid 1.0 N LiOH (1.1 mL, 1.1 mmol) was added dropwise to a mixture of methyl (±)-7-[[(6-amino-3-pyridinyl)amino]carbonyl]-3-oxo-4-(2-phenylethyl)-2,3,4,5-tetrahydro-1H-1,4-benzodiazepine-2-acetate (0.23 g, 0.48 mmol) in THF (12 mL) and H$_2$O (17 mL) at RT. After 22.5 h, the dark reddish-brown reaction mixture was concentrated on the rotavap to remove excess THF. The resulting reddish solution was cooled in an ice-bath, and neutralized with 1.0 N AcOH (1.8 mL). The precipitate was collected by suction filtration, washed with water and ether, and air-dried to give the title compound (0.19 g, 86%) as a pinkish-purple solid: $^1$H NMR (400 MHz, DMSO-d$_6$) δ9.55 (s, 1H), 6.40–8.29 (m, 7H), 5.69 (s, 2H), 5.42 (d, J=17 Hz, 1H), 5.09 (br, 1H), 3.95 (dd, J=17,1H), 3.59–3.65 (m, 2H), 2.51–2.82 (m, 4H); MS (ES) m/e 460.2 (M+H)$^+$. Anal. Calcd for C$_{25}$H$_{25}$N$_5$O$_4$.9/4 H$_2$O: C, 60.05; H, 5.98; N, 14.01. Found: C, 59.79; H, 5.92; N, 13.64.

Example 4

Preparation of (±)-1-Acetyl-7-[[(6-amino-2-pyridinyl)amino]carbonyl]-4-methyl-3-oxo-2,3,4,5-tetrahydro-1H-1,4-benzodiazepine-2-acetic acid a) Methyl (±)-1-acetyl-7-carboxy-4-methyl-3-oxo-2,3,4,5-tetrahydro-1H-1,4-benzodiazepine-2-acetate Methyl (±)-7-carboxy-4-methyl-3-oxo-2,3,4,5-tetrahydro-1H-1,4-benzodiazepine-2-acetate (2.0 g, 8.6 mmol), acetic anhydride (25 mL) and acetic acid (1 mL) were heated to reflux. After 48 h, the reaction was concentrated, and the residue was diluted with H$_2$O (20 mL) and MeOH (15 mL). The resulting solution was concentrated to give the tide compound (1.8 g, 78%): $^1$H NMR (400 MHz, DMSO-d$_6$) δ1.7–1.8 (s, 3H), 2.2–2.6 (m, 2H), 2.9–3.0 (s, 3H), 3.5–3.6 (s, 3H), 4.2–4.3 (d, 1H), 4.7–4.8 (d, 1H), 5.8–5.9 (t, 1H), 7.5–7.6 (d, 1H), 7.9–8.0 (dd, 1H), 8.1–8.2 (d, 1H); MS (ES) m/e 335.0 (M+H)$^+$.

b) Methyl (±)-1-acetyl-7-[[(6-amino-2-pyridinyl) amino]carbonyl]-4-methyl-3-oxo-2,3,4,5-tetrahydro-1H-1,4-benzodiazepine-2-acetate HOBT.H$_2$O (0.54 g, 3.6 mmol) and EDC (0.686 g, 3.6 mmol) were added to a solution of methyl (±)-1-acetyl-7-carboxy-4-methyl-3-oxo-2,3,4,5-tetrahydro-1H-1,4-benzodiazepine-2-acetate (1.0 g, 3 mmol) in dry DMF (15 mL). After 1 h the reaction solution was added dropwise to a solution of 2,6-diaminopyridine (0.326 g, 3.0 mmol) in dry DMF (20 mL). The reaction solution was stirred for 18 h, then was concentrated. Chromatography (silica gel, 9:1 CH$_2$Cl$_2$/MeOH) gave the title compound (0.9 g, 70%): $^1$H NMR (400 MHz, DMSO-d$_6$) δ1.80 (s, 3H), 2.3–2.7 (m, 2H), 3.0–3.1 (s, 3H), 3.5–3.6 (s, 3H), 4.1–4.2 (d, 1H), 4.7–4.8 (d, 1H), 5.7–5.9 (m, 3H), 6.2–6.3 (d, 1H), 7.3–7.5 (m, 3H), 8.0–8.1 (d, 1H), 8.2–8.3 (s, 1H); MS (ES) m/e 426.0 (M+H)$^+$.

c) (±)-1-Acetyl-7-[[(6-amino-2-pyridinyl)amino] carbonyl]-4-methyl-3-oxo-2,3,4,5-tetrahydro-1H-1, 4-benzodiazepine-2-acetic acid 1 N NaOH (1.0 mL, 1.0 mmol) was added to a cold solution of methyl (±)-1-acetyl-7-[[(6-amino-2-pyridinyl) amino]carbonyl]-4-methyl-3-oxo-2,3,4,5-tetrahydro-1H-1, 4-benzodiazepine-2-acetate (0.23 g, 0.54 mmol), MeOH (2 mL) and H$_2$O (1 mL). The solution was stirred at room temperature for 18 h then was concentrated. Chromatography (ODS, 10% CH$_3$CN/H$_2$O-0.1% TFA) gave the title compound (0.215 g, 90%): $^1$H NMR (400 MHz, DMSO-d$_6$) δ1.7–1.9 (s, 3H), 2.0–2.6 (m, 2H), 3.0–3.1 (s, 3H), 4.1–4.2 (d, 1H), 4.7–4.8 (d, 1H), 5.7–5.9 (m, 1H), 6.4–6.5 (d, 1H), 7.0–7.1 (d, 1H), 7.5–7.6 (d, 1H), 7.6–7.8 (t, 1H), 8.0–8.1 (d, 1H), 8.2–8.3 (s, 1H); MS (ES) m/e 412.2 (M+H)$^+$. Anal. Calcd for C$_{20}$H$_{21}$N$_5$O$_5$.2.75 CF$_3$CO$_2$H: C, 42.25; H, 3.30; N, 9.66. Found: C, 42.01; H, 3.25; N, 9.85.

Example 5

Preparation of (±)-2-methyl-3-oxo-8-[[2-(pyridinyl) carbonyl]amino]-2,3,4,5-tetrahydro-1H-2-benzazepine-4-acetic acid a) Methyl (±)-8-amino-2-methyl-3-oxo-2,3,4,5-tetrahydro-1H-2-benzazepine-4-acetate A mixture of methyl (±)-8-[(benzyloxycarbonyl)amino]-2-methyl-3-oxo-2,3,4,5-tetrahydro-1H-2-benzazepine-4-acetate (1.5 g), Pearlman's catalyst (0.30 g), and warm AcOH (300 mL) was stirred under H$_2$ (balloon pressure). After 90 min, the mixture was filtered to remove the catalyst, and the filtrate was concentrated to give the title compound as a viscous oil (1 g, 100%): $^1$H NMR (CDCl$_3$) δ7.00 (br s, 2H), 6.88 (d, J=8.1 Hz, 1H), 6.57 (dd, J=8.1, 2.3 Hz, 1H), 6.43 (d, J=2.3 Hz, 1H), 5.25 (d, J=16.3 Hz, 1H), 3.78 (m, 1H), 3.70 (s, 3H), 3.68 (d, J=16.3 Hz, 1H), 3.03 (s, 3H), 3.00–2.80 (m, 3H), 2.40 (dd, J=16.7, 5.3 Hz, 1H).

b) Methyl (±)-2-methyl-3-oxo-8-[[2-(pyridinyl) carbonyl]amino]-2,3,4,5-tetrahydro-1H-2-benzazepine-4-acetate To a solution stirred under argon at room temperature of methyl (±)-8-carboxy-2-methyl-3-oxo-2,3,4,5-tetrahydro- 1H-2-benzazepine-4-acetate (0.30 g, 1 mmole), picolinic acid (1.2 mmole), HOBT.H$_2$O (0.17 g, 1.2 mmole), diisopropylethylamine (0.53 g, 4 mmole), and DMF (5 mL) was added EDC (0.24 g, 1.2 mmole). The resulting mixture was stirred for 18 h, then was concentrated to dryness, and the residue was partitioned between EtOAc and H$_2$O. The organic phase was washed with H$_2$O and brine, dried (MgSO$_4$), and concentrated. Purification by chromatography (silica gel, 1–5% MeOH/CH$_2$Cl$_2$) gave the title compound as an amorphous solid (26%): $^1$H NMR (CDCl$_3$) δ10.02 (s, 1H), 8.62 (d, J=4.1 Hz, 1H), 8.29 (d, J=7.8 Hz, 1H), 7.93 (m, 1H), 7.79 (d, J=2.1 Hz, 1H), 7.50 (m, 2H), 7.11 (d, J=8.3 Hz, 1H), 5.33 (d, J=16.6 Hz, 1H), 3.88 (d, J=16.6 Hz, 1H), 3.85 (m, 1H), 3,72 (s, 3H), 3.06 (s, 3H), 3.00–2.85 (m, 3H), 2.43 (dd, J=16.7, 5.4 Hz, 1H).

c) (±)-2-Methyl-3-oxo-8-[[2-(pyridinyl)carbonyl]amino]-2,3,4,5-tetrahydro-1H-2-benzazepine-4-acetic acid A solution of methyl (±)-8-amino-2-methyl-3-oxo-2,3,4,5-tetrahydro-1H-2-benzazepine-4-acetate (0.054 g), LiOH H$_2$O (0.008 g), THF (2 mL), and H$_2$O (2 mL) was stirred at RT. After 18 h, the reaction was concentrated to dryness and the residue was dissolved in H$_2$O. The solution was brought to pH 5 with 3N HCl, and the resulting precipitate was collected by filtration. Drying under vacuum gave the title compound as a colorless solid (0.04 g, 77%): $^1$H NMR (DMSO-d$_6$) δ8.77 (d, J=4 Hz, 1H), 8.24 (d, J=8 Hz, 1H), 8.10 (m, 1H), 7.88 (d, J=2 Hz, 1H), 7.80–7.70 (m, 2H), 7.15 (d, J=8 Hz, 1H), 5.35 (d, J=16 Hz, 1H), 4.00 (d, J=16 Hz, 1H), 3.82 (m 1H), 2.97 (s, 3H), 2.78 (m, 2H), 2.55 (m, 1H), 2.38 (dd, J=16, 5 Hz, 2H); MS (ES) m/e354 (M+H)$^+$. Anal. Calcd for C$_{19}$H$_{19}$N$_3$O$_4$.0.125 H$_2$O: C, 64.17; H, 5.46; N, 11.82. Found: C, 63.99; H, 5.39; N, 11.77.

Example 6

Preparation of (±)-8-[(benzyloxycarbonyl)amino]-2-methyl-3-oxo-2,3,4,5-tetrahydro-1H-2-benzazepine-4-acetic acid a) Methyl (±)-8-[(benzyloxycarbonyl)amino]-2-methyl-3-oxo-2,3,4,5-tetrahydro-1H-2-benzazepine-4-acetate To a solution stirred under argon at room temperature of methyl (±)-8-carboxy-2-methyl-3-oxo-2,3,4,5-tetrahydro-2-benzazepine-4-acetate (0.30 g, 1 mmol) and triethylamine (0.16 mL, 1.2 mmol) in toluene was added diphenylphosphorylazide (0.31 g, 1.2 mmol). The resulting mixture was heated at 80° C. for 1 h, then was allowed to cool, and benzyl alcohol (0.22 g, 2 mmol) was added. The mixture was heated at 80° C. for 4 h, then was concentrated to remove the toluene. The residue was dissolved in EtOAc, and the solution was washed sequentially with 5% aqueous NaHCO$_3$, 1N HCl, and brine. Drying (MgSO$_4$), concentration, and chromatography (silica gel, 1% MeOH/CH$_2$Cl$_2$) gave the title compound as a colorless solid (0.20 g, 47%): $^1$H NMR (CDCl$_3$) δ7.40–7.30 (m, 6H), 7.06 (dd, J=8.3, 2 Hz, 1H), 7.02 (d, J=8.3 Hz, 1H), 6.65 (br s, 1H), 5.28 (d, J=16.7 Hz, 1H), 5.20 (s, 2H), 3.80 (m, 1H), 3.79 (d, J=16.7 Hz, 1H), 3.70(s, 3H), 3.03 (s, 3H), 3.00 (m, 2H), 2.88 (m, 1H), 2.41 (dd, J=16.8, 5.3, 1H).

b) (±)-8-[(Benzyloxycarbonyl)amino]-2-methyl-3-oxo-2,3,4,5-tetrahydro-1H-2-benzazepine-4-acetic acid A solution of the compound of Example 6(a) (0.24 mmol), LiOH.H$_2$O (0.013 g, 0.31 mmole), THF (2 mL), and H$_2$O (2 mL) was stirred at RT for 18 h, then was concentrated to dryness. The residue was dissolved in H$_2$O, and the solution was brought to pH 4–5 with 3N HCl. The resulting precipitate was collected by filtration and dried to yield the title compound (83%): $^1$H NMR (Acetone-d$_6$) δ8.50 (br s, 1H), 7.45 (br s, 1H), 7.40–7.30 (m, 5H), 7.05 (d, J=8.3 Hz, 1H), 5.31 (d, J=16.4 Hz, 1H), 5.17 (s, 2H), 3.90 (d, J=16.5 Hz, 1H), 3.84 (m, 1H), 3.08 (dd, J=11.6, 4.9 Hz, 1H); MS (ES) m/e 383.2 (M+H)$^+$. Anal. Calcd for C$_{21}$H$_{22}$N$_2$O$_5$.0.25 H$_2$O: C, 65.19; H, 5.86; N, 7.24. Found: C, 65.45; H, 5.90; N, 7.27.

Example 7

Preparation of (±)-7-[[[3-(aminoiminomethyl)phenyl]amino]carbonyl]-4-methyl-3-oxo-2,3,4,5-tetrahydro-1H-1,4-benzodiazepine-2-acetic acid a) Methyl (±)-7-[[[3-[N-(benzyloxycarbonyl)aminoiminomethyl]phenyl]amino]carbonyl]-4-methyl-3-oxo-2,3,4,5-tetrahydro-1H-1,4-benzodiazepine-2-acetic acid Following the procedure of Example 2(a), methyl (±)-7-carboxy-4-methyl-3-oxo-2,3,4,5-tetrahydro-1H-1,4-benzodiazepine-2-acetate was converted to the corresponding acid chloride. This was dissolved in CH$_2$Cl$_2$ (10 mL) and added dropwise to a solution of 3-amino-(N-benzyloxycarbonyl)benzamidine (1.48 g, 5.46 mmol) and pyridine (0.72 g, 9.1 mmol) in CH$_2$Cl$_2$ (15 mL) at 0° C. under argon. The mixture was stirred in RT for 2 h, then was partitioned between CH$_2$Cl$_2$, EtOAc and 5% NaHCO$_3$. The organic layer was separated and washed with 0.05 N HCl, which gave a precipitate. This was collected and recrystallized from MeOH/CH$_2$Cl$_2$/EtOAc to afford the title compound (0.5 g, 51%): $^1$H NMR (400 MHz, CDCl$_3$/DMSO-d$_6$) δ6.64–10.63 (m, 12H), 5.55 (d, J=16 Hz, 1H), 5.38 (s, 2H), 5.19 (m, 1H), 3.86 (d, J=17 Hz, 1H), 3.61 (s, 3H), 3.02 (s, 3H), 2.93 (dd, J=17, 9 Hz, 1H), 2.66 (dd, J=17, 4 Hz, 1H).

b) Methyl (±)-7-[[[3-(aminoiminomethyl)phenyl]amino]carbonyl]-4-methyl-3-oxo-2,3,4,5-tetrahydro-1H-1,4-benzodiazepine-2-acetic acid A mixture containing the compound of Example 7(a), 10% Pd/C (0.19 g), and MeOH (30 mL) was hydrogenated at 45 psi in a Parr apparatus. After 2 h, glacial AcOH (5 mL) and more 10% Pd/C (0.15 g) were added, and hydrogenation at 45 psi was continued for an additional 70 min. The reaction mixture was filtered through a bed of Celite® and concentrated to give the title compound (0.21 g, 81%) as a white solid: $^1$H NMR (250 MHz, DMSO-d$_6$) δ6.55–10.19 (m, 10H), 5.55 (d, J=16 Hz, 1H), 5.18 (m, 1H), 3.90 (d, J=17 Hz, 1H), 3.62 (s, 3H), 2.97 (s, 3H), 2.86 (dd, J=17, 9 Hz, 1H), 2.67 (dd, J=17, 5 Hz, 1H); MS (ES) m/e 410.2 (M+H)$^+$.

c) (±)-7-[[[3-(Aminoiminomethyl)phenyl]amino]carbonyl]-4-methyl-3-oxo-2,3,4,5-tetrahydro-1H-1,4-benzodiazepine-2-acetic acid Following the procedure of Example 2(b), the compound of Example 7(b) was saponified and purified to give the title compound: $^1$H NMR (250 MHz, DMSO-d$_6$) δ6.51–9.30 (m, 10H), 5.54 (d, J=17 Hz, 1H), 5.14 (m, 1H), 3.88 (d, J=17 Hz, 1H), 2.98 (s, 3H), 2.82 (dd, J=17, 9 Hz, 1H), 2.57 (dd, J=17, 5 Hz, 1H); MS (ES) m/e 396.2 (M+H)$^+$. Anal. Calcd for C$_{20}$H$_{21}$N$_5$O$_4$.3/2 CF$_3$CO$_2$H: C, 48.77; H, 4.00; N, 12.36. Found: C, 48.77; H, 4.38; N, 12.52.

Example 8

Preparation of (±)-7-[[[3-(aminocarbonyl)phenyl]amino]carbonyl]-4-methyl-3-oxo-2,3,4,5-tetrahydro-1H-1,4-benzodiazepine-2-acetic acid The title compound was isolated as a minor product from the reaction described in Example 7(c): $^1$H NMR (250 MHz, DMSO-d$_6$) δ9.91 (s, 1H), 6.42–8.25 (m, 9H), 5.53 (d, J=17 Hz, 1H), 5.12 (m, 1H), 3.87 (d, J=17 Hz, 1H), 2.98 (s, 3H), 2.82 (dd, J=17, 9 Hz, 1H), 2.57 (dd, J=17, 5 Hz, 1H); MS (ES) m/e 397.0 (M+H)$^+$. Anal. Calcd for C$_{20}$H$_{20}$N$_5$O$_5$.1/3 CF$_3$CO$_2$H.2/3 H$_2$O: C, 55.60; H, 4.89; N, 12.55. Found: C, 55.38; H, 5.05; N, 12.42.

Example 9

Preparation of (±)-4-methyl-3-oxo-7-[1-(4-phenylpiperazinyl)carbonyl]-2,3,4,5-tetrahydro-1H-1,4-benzodiazepine-2-acetic acid a) Methyl (±)-4-methyl-3-oxo-7-[1-(4-phenylpiperazinyl)carbonyl]-2,3,4,5-tetrahydro-1H-1,4-benzodiazepine-2-acetate EDC (137.6 mg, 0.72 mmol) was added to a solution of methyl (±)-7-carboxy-4-methyl-3-oxo-2,3,4,5-tetrahydro-1H-1,4-benzodiazepine-2-acetate (175.4 mg, 0.6 mmol), 4-phenylpiperazine (0.11 mL, 0.72 mmol), HOBT.H$_2$O (97.3 mg, 0.72 mmol), and diisopropylethylamine (0.21 mL, 1.2 mmol) in anhydrous DMF (3 mL) at RT. After 18 h, the reaction was concentrated on the rotavap (high vacuum), and the residue was diluted with H$_2$O. CHCl$_3$ extraction drying (Na$_2$SO$_4$), concentration, and reconcentration from xylenes left a yellow oil, which solidified on treatment with EtOAc followed by concentration. Chromatography (silica gel, 5% MeOH/CHCl$_3$) gave an oil which was treated with EtOAc to afford a solid. Trituration with cold Et$_2$O (2×20 mL) gave the title compound as an off-white solid (238.8 mg, 91%): TLC R$_f$ (5% MeOH/CHCl$_3$) 0.33; $^1$H NMR (250 MHz, CDCl$_3$) δ7.07–7.36 (m, 4H), 6.82–7.00 (m, 3H), 6.49–6.59 (m, 1H), 5.45 (d, J=16.5 Hz, 1H), 5.19 (app t, 1H), 3.55–3.95 (m, 5H), 3.75 (s, 3H), 3.15–3.35 (m, 4H), 3.09 (s, 3H), 3.00 (dd, J=16.0, 6.6 Hz, 1H), 2.67 (dd, J=16.0, 6.5 Hz, 1H); MS (ES) m/e 437.2 (M+H)$^+$, 275.0.

b) (±)-4-Methyl-3-oxo-7-[1-(4-phenylpiperazinyl)carbonyl]-2,3,4,5-tetrahydro-1H-1,4-benzodiazepine-2-acetic acid A mixture of methyl (±)-4-methyl-3-oxo-7-[1-(4-phenylpiperazinyl)carbonyl]-2,3,4,5-tetrahydro-1H-1,4-benzodiazepine-2-acetate (238.8 mg, 0.55 mmol), 1.0 N NaOH (1.7 mL, 1.7 mmol), and MeOH (5.5 mL) was stirred at 35° C. overnight. The resulting homogeneous solution was concentrated to dryness, and the residue was dissolved in 1:1 H$_2$O/CH$_3$CN. The solution was cooled to 0° C. and acidified with TFA, then was concentrated to a pinkish-orange oil. Chromatography (ODS, 25% CH$_3$CN/H$_2$O-0.1% TFA), concentration, and lyophilization gave the title compound (213.1 mg, 69%) as an off-white powder: HPLC k' 2.6 (PRP-1®, 25% CH$_3$CN/H$_2$O-0.1% TFA); $^1$H NMR (400 MHz, CD$_3$OD) δ7.29–7.40 (m, 2H), 7.12–7.22 (m, 4H), 7.04 (t, J=7.4 Hz, 1H), 6.63 (d, J=9.1 Hz, 1H), 5.58 (d, J=16.5 Hz, 1H), 5.20 (dd, J=9.0, 5.1 Hz, 1H), 3.78–3.95 (m, 5H), 3.23–3.39 (m, 4 H, partially obscured by residual solvent signal), 3.04 (s, 3H), 2.94 (dd, J=16.8, 9.0 Hz, 1H), 2.65 (dd, J=16.8, 5.1 Hz, 1H); MS (ES) m/e 423.2 (M+H)$^+$, 261.0. Anal. Calcd for C$_{23}$H$_{26}$N$_4$O$_4$.1.25 CF$_3$CO$_2$H: C, 54.20: H, 4.86; N, 9.92. Found: C, 54.42; H, 4.98; N, 10.00.

Example 10

Preparation of (±)-4-methyl-3-oxo-7-[(1-piperazinyl)carbonyl]-2,3,4,5-tetrahydro-1H-1,4-benzodiazepine-2-acetic acid a) Methyl (±)-4-methyl-3-oxo-7-[1-[4-(tert-butoxycarbonyl)piperazinyl]carbonyl]-2,3,4,5-tetrahydro-1H-1,4-benzodiazepine-2-acetate EDC (137.6 mg, 0.72 mmol) was added to a solution of methyl (±)-7-carboxy-4-methyl-3-oxo-2,3,4,5-tetrahydro-1H-1,4-benzodiazepine-2-acetate (175.4 mg, 0.6 mmol), 4-(tert-butoxycarbonyl)piperazine (0.21 g, 1.2 mmol), HOBT.H$_2$O (97.3 mg, 0.72 mmol), and diisopropylethylamine (0.21 mL, 1.2 mmol) in anhydrous DMF (3 mL) at RT. After 17 h, the reaction was concentrated on the rotavap (high vacuum), and the residue was partitioned between 10% Na$_2$CO$_3$ and CH$_2$Cl$_2$. The layers were separated and the aqueous layer was extracted with CH$_2$Cl$_2$. Drying (Na$_2$SO$_4$) and concentration left a residue which was reconcentrated from xylenes to remove DMF. Chromatography (silica gel, 10% MeOH in 1:1 EtOAc/CHCl$_3$) gave the title compound as a colorless foam (266 mg, 96%): TLC R$_f$ 0.54 (10% MeOH in 1:1 EtOAc/CHCl$_3$); $^1$H NMR (250 MHz, CDCl$_3$) δ7.09–7.16 (m, 2H), 6.53 (d, J=8.9 Hz, 1H), 5.44 (d, J=16.5 Hz, 1H), 5.07 (t, J=6.6 Hz, 1H), 3.75 (s, 3H), 3.73 (d, J=16.5 Hz, 1H, partially obscured by the δ3.75 resonance), 3.32–3.68 (m, 8H), 3.08 (s, 3H), 2.99 (dd, J=16.0, 6.7 Hz, 1H), 2.67 (dd, J=16.0, 6.4 Hz, 1H), 1.47 (s, 9H); IR (CHCl$_3$) 3240–3560 (br), 1729, 1685 (shoulder), 1665, 1610, 1455, 1437, 1420, 1410, 1367, 1288, 1263, 1245, 1168, 1123 cm$^{-1}$; MS (ES) m/e 461.2 (M+H)$^+$, 405.2 (M+H–C$_4$H$_8$)$^+$.

b (±)-4-Methyl-3-oxo-7-[(1-piperazinyl)carbonyl]-2,3,4,5-tetrahydro-1H-1,4-benzodiazepine-2-acetic acid TFA (2.9 mL) was added all at once to a solution of methyl (±)-4-methyl-3-oxo-7-[1-[4-(tert-butoxycarbonyl)piperazinyl]carbonyl]-2,3,4,5-tetrahydro-1H-1,4-benzodiazepine-2-acetate (266.2 mg, 0.58 mmol) in anhydrous CH$_2$Cl$_2$ (2.9 mL) at 0° C., and the reaction was warmed to RT. After 2 h, the reaction was concentrated and the residue was reconcentrated several times from 1:1 toluene/MeOH to remove residual TFA. The resulting yellow oil was dissolved in MeOH (5.8 mL) and cooled to 0° C. 1.0 N NaOH (2.9 mL, 2.9 mmol) was added, and the bright yellow solution was stirred at RT. After 20 h, the reaction was concentrated and the residue was dissolved in H$_2$O (5 mL). The solution was acidified with TFA and concentrated to leave a light yellow oil. Chromatography (ODS, 5% CH$_3$CN/H$_2$O 0.1% TFA), concentration, and lyophilization gave the title compound as a light yellow powder (206.1 mg, 66%): HPLC k' 2.2 (PRP-1 ®, 7% CH$_3$CN/H$_2$O-0.1% TFA); $^1$H NMR (400 MHz, CD$_3$OD) δ7.15–7.23 (m, 2H), 6.59–6.65 (m, 1H), 5.58 (d, J=16.5 Hz, 1H), 5.20 (dd, J=9.0, 5.1 Hz, 1H), 3.81–3.95 (m, 5H), 3.22–3.30 (m, 4H), 3.04 (s, 3H), 2.94 (dd, J=16.7, 9.0 Hz, 1H), 2.65 (dd, J=16.7, 5.1 Hz, 1H); MS (ES) m/e 347.2 (M+H)$^+$, 261.0. Anal. Calcd for C$_{17}$H$_{22}$N$_4$O$_4$.1.5 CF$_3$CO$_2$H.H$_2$O: C, 44.86; H, 4.80; N, 10.46. Found: C, 44.82; H, 4.82; N, 10.36.

Example 11

Preparation of (±)-4-methyl-3-oxo-7-[1-[4-(1-piperidinyl)piperidinyl]carbonyl]-2,3,4,5-tetrahydro-1H-1,4-benzodiazepine-2-acetic acid a) Methyl (±)-4-methyl-3-oxo-7-[1-[4-(1-piperidinyl)piperidinyl]carbonyl]-2,3,4,5-tetrahydro-1H-1,4-benzodiazepine-2-acetate EDC (138 mg, 0.72 mmol) was added to a solution of methyl (±)-7-carboxy-4-methyl-3-oxo-2,3,4,5-tetrahydro-1H-1,4-benzodiazepine-2-acetate (175 mg, 0.6 mmol), 4-(1-piperidinyl)piperidine (121.2 mg, 0.72 mmol), HOBT.H$_2$O (97 mg, 0.72 mmol), and diisopropylethylamine (0.21 mL, 1.2 mmol) in anhydrous DMF (3 mL) at RT. After 21 h, the reaction was concentrated on the rotavap (high vacuum), and the residue was taken up in CH$_2$Cl$_2$ and washed with H$_2$O. Drying (Na$_2$SO$_4$) and concentration left the crude product as an off-white solid, which was reconcentrated from xylenes to remove residual DMF. The aqueous washings were combined and extracted with CHCl$_3$. The combined CHCl$_3$ layers were dried (Na$_2$SO$_4$), concentrated, and reconcentrated from xylenes to provide additional crude product. The crude products were combined and chromatographed (silica (el, 20% MeOH/CHCl$_3$) to give the title compound as a colorless solid (205.2 mg, 77%): TLC R$_f$ 0.39 (20% MeOH/CHCl$_3$); $^1$H NMR (250 MHz, CDCl$_3$) δ7.05–7.15 (m, 2H), 6.52 (d, J=8.8 Hz, 1H), 5.44 (d, J=16.4 Hz, 1H), 5.00–5.12 (m, 1H), 4.10–4.70 (m, 2H), 4.40 (d, J=5.1 Hz, 1H), 3.75 (s, 3H), 3.73 (d, J=16.4 Hz, 1 H, partially obscured by the δ3.75 resonance), 3.08 (s, 3H), 2.40–3.20 (m, 9H), 1.35–2.10 (m, 10H); IR (CHCl$_3$) 3400, 2930, 1731, 1669, 1613, 1439, 1282 cm$^{-1}$; MS (ES) m/e 443.2 (M+H)$^+$.

b) (±)-4-Methyl-3-oxo-7-[1-[4-(1-piperidinyl) piperidinyl]carbonyl]-2,3,4,5-tetrahydro-1H-1,4-benzodiazepine-2-acetic acid A mixture of methyl (±)-4-methyl-3-oxo-7-[1-[4-(1-piperidinyl)piperidinyl]carbonyl]-2,3,4,5-tetrahydro-1H-1,4-benzodiazepine-2-acetate (205.2 mg, 0.48 mmol), 1.0 N NaOH (1.4 mL, 1.4 mmol), and MeOH (4.8 mL) was stirred at 35–40° C. for 19.5 h, then was concentrated to dryness. The residue was dissolved in H$_2$O (2–3 mL), cooled to 0° C., and acidified with TFA. Concentration left a residue which was purified by chromatography (ODS, step gradient, 12% CH$_3$CN/H$_2$O-0.1% TFA, 15% CH$_3$CN/H$_2$O-0.1% TFA). Concentration and lyophilization gave the title compound as a colorless powder (229.1 mg, 78%): HPLC k' 2.9 (PRP-1®, 12% CH$_3$CN/H$_2$O-0.1% TFA); $^1$H NMR (400 MHz, CD$_3$OD) δ7.11–7.18 (m, 2H), 6.61 (d, J=9.0 Hz, 1H), 5.58 (d, J=16.6 Hz, 1H), 5.20 (dd, J=9.0, 5.1 Hz, 1H), 4.25–4.68 (m, 2H), 3.88 (d, J=16.6 Hz, 1H), 3.41–3.56 (m, 3H), 3.04 (s, 3H), 2.88–3.16 (m, 4H), 2.94 (dd, J=16.7, 9.0 Hz, 1H), 2.65 (dd, J=16.7, 5.1 Hz, 1H), 1.43–2.20 (m, 10H); MS (ES) m/e 429.2 (M+H)$^+$. Anal. Calcd for C$_{23}$H$_{32}$N$_4$O$_4$·1.5 CF$_3$CO$_2$H·0.5 H$_2$O: C, 51.31; H, 5.71; N, 9.21. Found: C, 51.51; H, 5.90; N, 9.29.

Example 12

Preparation of (±)-4-methyl-3-oxo-7-[1-[4-(2-pyridinyl)piperazinyl]carbonyl]2,3,4,5-tetrahydro-1H-1,4-benzodiazepine-2-acetic acid a) Methyl (±)-4-methyl-3-oxo-7-[1-[4-(2-pyridinyl) piperazinyl]carbonyl]-2,3,4,5-tetrahydro-1H-1,4-benzodiazepine-2-acetate EDC (137.6 mg, 0.72 mmol) was added to a solution of methyl (±)-7-carboxy-4-methyl-3-oxo-2,3,4,5-tetrahydro-1H-1,4-benzodiazepine-2-acetate (175.4 mg, 0.6 mmol), 4-(2-pyridinyl)piperazine (0.11 mL, 0.72 mmol), HOBT·H$_2$O (97.3 mg, 0.72 mmol), and diisopropylethylamine (0.21 mL, 1.2 mmol) in anhydrous DMF (3 mL) at RT. After 18.5 h, the mixture was concentrated on the rotavap (high vacuum), and the residue was partitioned between 10% aqueous Na$_2$CO$_3$ and CHCl$_3$. The layers were separated and the aqueous layer was extracted with CHCl$_3$. The combined CHCl$_3$ layers were washed with brine, dried (Na$_2$SO$_4$), and concentrated. The residue was concentrated from 1:1:1 CHCl$_3$/MeOH/xylenes to remove DMF, then was chromatographed (silica gel, 5% MeOH/CHCl$_3$). The impure oily product obtained in this way was dissolved in EtOAc. Crystallization began almost immediately, and the mixture was cooled in ice. The solid was collected by suction filtration and was washed with EtOAc. Drying in high vacuum gave the title compound as a nearly colorless solid (239.6 mg, 91%): mp >250° C.; TLC R$_f$ 0.39 (5% MeOH/CHCl$_3$); $^1$H NMR (400 MHz, CDCl$_3$) δ8.18–8.25 (m, 1H), 7.49–7.59 (m, 1H), 7.15–7.23 (m, 2H), 6.65–6.75 (m, 2H), 6.54 (d, J=8.0 Hz, 1H), 5.45 (d, J=16.5 Hz, 1H), 5.03–5.12 (m, 1H), 4.40 (d, J=5.0 Hz, 1H), 3.68–3.85 (m, 5H), 3.75 (s, 3H), 3.51–3.68 (m, 4H), 3.09 (s, 3H), 3.00 (dd, J=16.0, 6.6 Hz, 1H), 2.68 (dd, J=16.0, 6.5 Hz, 1H); MS (ES) m/e 438.2 (M+H)$^+$, 275.0.

b) (±)-4-Methyl-3-oxo-7-[1-[4-(2-pyridinyl) piperazinyl]carbonyl]-2,3,4,5-tetrahydro-1H-1,4-benzodiazepine-2-acetic acid 1.0 N NaOH (0.65 mL, 0.65 mmol) was added dropwise to a suspension of methyl (±)-4-methyl-3-oxo-7-[1-[4-(2-pyridinyl)piperazinyl]carbonyl]-2,3,4,5-tetrahydro-1H-1,4-benzodiazepine-2-acetate (235 mg, 0.54 mmol) in MeOH (5.4 mL) at RT, and the resulting mixture was stirred at 50° C. After 3.5 h, more 1.0 N NaOH (0.65 mL, 0.65 mmol) was added, and warming at 50° C. was continued for 0.5 h. The resulting homogeneous solution was stirred at RT for 18.5 h, then was concentrated. The residue was dissolved in H$_2$O (5 mL), and the solution was acidified with TFA. Concentration left a foamy oil which was purified by chromatography (ODS, 12% CH$_3$CN/H$_2$O-0.1% TFA). Concentration and lyophilization gave the title compound (280 mg, 87%) as a colorless powder: HPLC k' 3.7 (PRP-1®, 12% CH$_3$CN/H$_2$O-0.1% TFA); $^1$H NMR (400 MHz, CD$_3$OD) δ7.96–8.10 (m, 2H), 7.37 (d, J=9.1 Hz, 1H), 7.28–7.38 (m, 2H), 7.02 (app t, 1H), 6.64 (d, J=9.1 Hz, 1H), 5.58 (d, J=16.5 Hz, 1H), 5.21 (dd, J=9.0, 5.1 Hz, 1H), 3.68–3.97 (m, 9H), 3.04 (s, 3H), 2.94 (dd, J=16.8, 9.0 Hz, 1H), 2.66 (dd, J=16.8, 5.1 Hz, 1H); MS (ES) m/e 424.2 (M+H)$^+$. Anal. Calcd for C$_{22}$H$_{25}$N$_5$O$_4$· 1.5 CF$_3$CO$_2$H: C, 50.51; H, 4.49; N, 11.78. Found: C, 50.42; H, 4.78; N, 11.77.

Example 13

Preparation of (±)-4-methyl-3-oxo-7-[1-[4-(phenylmethyl)piperazinyl]carbonyl]2,3,4,5-tetrahydro-1H-1,4-benzodiazepine-2-acetic acid a) Methyl (±)-4-methyl-3-oxo-7-[1-[4-(phenylmethyl)piperazinyl]carbonyl]-2,3,4,5-tetrahydro-1H-1,4-benzodiazepine-2-acetate Methyl (±)-7-carboxy-4-methyl-3-oxo-2,3,4,5-tetrahydro-1H-1,4-benzodiazepine-2-acetate (292.3 mg, 1.0 mmol) was refluxed with thionyl chloride (10 mL) for 20 min, and the yellow solution was concentrated. The residue was concentrated from dry toluene (5 mL), then was taken up in dry CH$_2$Cl$_2$ (10 mL) and cooled to 0° C. under argon. 1-benzylpiperazine (0.70 mL, 4 mmol) was added all at once, and after 5 min, the light yellow solution was warmed to RT. The reaction was stirred for 0.5 h, then was washed sequentially with 1.0 N NaOH and H$_2$O. Drying (MgSO4). concentration, and chromatography (silica gel, 10% MeOH in 1:1 EtOAc/CHCl$_3$) gave the title compound as an off-white foam (344.4 mg, 76%): TLC R$_f$ 0.47 (10% MeOH in 1:1 EtOAc/CHCl$_3$); $^1$H NMR (400 MHz, CDCl$_3$) δ7.22–7.40 (m, 5H), 7.08–7.20 (m, 2H), 6.50 (d, J=8.8 Hz, 1H), 5.43 (d, J=16.4 Hz, 1H), 5.02–5.10 (m 1H), 4.37 (br d, J=5.1 Hz, 1H), 3.45–3.85 (m, 7H), 3.74 (s, 3H), 3.07 (s, 3H), 2.98 (dd, J=16.1, 6.7 Hz, 1H), 2.66 (dd, J=16.1, 6.4 Hz, 1H); FTIR (CCl$_4$) 1740, 1672, 1630, 1611, 1456, 1437, 1296 cm$^{-1}$; MS (ES) m/e 451.2 (M+H)$^+$.

b) (±)-4-Methyl-3-oxo-7-[1-[4-(phenylmethyl)piperazinyl]carbonyl]-2,3,4,5-tetrahydro-1H-1,4-benzodiazepine-2-acetic acid 1.0 N LiOH (0.91 mL, 0.91 mmol) was added to a solution of methyl (±)-4-methyl-3-oxo-7-[1-[4-(phenylmethyl)piperazinyl]carbonyl]-2,3,4,5-tetrahydro-1H-1,4-benzodiazepine-2-acetate (344.4 mg, 0.76 mmol) in THF (3.8 mL) and H$_2$O (2.9 mL) at 0° C. The resulting bright yellow solution was stirred at RT for 15 h, then was acidified with TFA (0.23 mL) and concentrated to dryness. Chromatography (ODS, 20% CH$_3$CN/H$_2$O-0.1% TFA), concentration, and lyophilization gave the title compound as a colorless powder (349.9 mg, 77%): HPLC k' 1.6 (PRP-1 ®, 20% CH$_3$CN/H$_2$O-0.1% TFA); $^1$H NMR (400 MHz, CD$_3$OD) δ7.43–7.57 (m, 5H), 7.14–7.22 (m, 2H), 6.62 (d, J=9.0 Hz, 1H), 5.57 (d, J=16.6 Hz, 1H), 5.20 (dd, J=9.0, 5.1 Hz, 1H), 4.37 (s, 2H), 3.88 (d, J=16.6 Hz, 1H), 3.45–4.30 (m, 2H), 3.15–3.45 (m, 6 H, partially obscured by residual solvent signal), 3.03 (s, 3H), 2.93 (dd, J=16.9, 9.0 Hz, 1H), 2.65 (dd, J=16.9, 5.1 Hz, 1H); MS (ES) m/e 437.2 (M+H)$^+$. Anal. Calcd for C$_{24}$H$_{28}$N$_4$O$_4$.1.25 CF$_3$CO$_2$H: C, 53.31; H, 5.28; N, 9.38. Found: C, 53.30; H, 5.42; N, 9.35.

Example 14

Preparation of (±)-4-methyl-3-oxo-7-[1-[4-(2-pyrmidinyl)piperazinyl]carbonyl]-2,3,4,5-tetrahydro-1H-1,4-benzodiazepine-2-acetic acid a) Methyl (±)-4-methyl-3-oxo-7-[1-[4-(2-pyrimidinyl)piperazinyl]carbonyl]-2,3,4,5-tetrahydro-1H-1,4-benzodiazepine-2-acetate A mixture of methyl (±)-7-carboxy-4-methyl-3-oxo-2,3,4,5-tetrahydro-1H-1,4-benzodiazepine-2-acetate (584 mg, 2.0 mmol), 1-(2-pyrimidinyl)piperazine dihydrochloride (522 mg, 2.2 mmol), HOBT.H$_2$O (270 mg, 2 mmol), triethylamine (1.0 mL, 7.2 mmol), and EDC (383 mg, 2 mmol) in anhydrous DMF (40 mL) was stirred at RT overnight. The reaction was concentrated in vacuum, and the resulting residue was diluted with 5% K$_2$CO$_3$.CH$_2$Cl$_2$ extraction, drying (MgSO$_4$), and concentration gave the title compound (0.76 g, 86%): MS (ES) m/e 483 (M+H)$^+$.

b) (±)-4-Methyl-3-oxo-7-[1-[4-(2-pyrimidinyl)piperazinyl]carbonyl]-2,3,4,5-tetrahydro-1H-1,4-benzodiazepine-2-acetic acid Methyl (±)-4-methyl-3-oxo-7-[1-[4-(2-pyrimidinyl)piperazinyl]carbonyl]-2,3,4,5-tetrahydro-1H-1,4-benzodiazepine-2-acetate (0.7 g, 1.6 mmol) was suspended in MeOH (10 mL) and THF (5 mL), and 1.0 N NaOH (6 mL) were added. The reaction was stirred at RT for 2 d, then was concentrated in vacuum. The residue was diluted with H$_2$O, and the pH was adjusted to 5 to 6 with 1.5 N HCl. Lyophilization gave the title compound (0.186 g, 27%): MS (ES) m/e 425 (M+H)$^+$. Anal. Calcd for C$_{21}$H$_{24}$N$_6$O$_4$.2.4H$_2$O: C, 53.93; H, 6.21; N, 17.97. Found: C, 54.25; H, 5.96; N, 17.53.

Example 15

Preparation of 8-[[2S-amino-3-phenylpropanoyl]amino]-2-methyl-3-oxo-2,3,4,5-tetrahydro-1H-2-benzazepine-4RS-acetic acid a) Methyl-8-[[2S-(tert-butoxycarbonyl)amino-3-phenylpropanoyl]amino]-2-methyl-3-oxo-2,3,4,5-tetrahydro-1H-2-benzazepine-4RS-acetate Methyl (±)-8-amino-2-methyl-3-oxo-2,3,4,5-tetrahydro-1H-2-benzazepine-4-acetate was coupled with Boc-L-phenylalanine according to the procedure of Example 5(b). Purification by chromatography (silica gel, 1%–5% CH$_3$OH/CH$_2$Cl$_2$) gave the title compound as a light yellow foam (99%): $^1$H NMR (CDCl$_3$) δ7.80 (m, 1H), 7.30 (m, 5H), 7.02 (m, 2H), 5.25 (d, J=15.9 Hz, 1H), 5.10 (m, 1H), 4.45 (m, 1H), 3.80 (m, 1H), 3.78 (d, J=15.9 Hz, 1H), 3.71 (s, 3H), 3.14 (d, J=6.8 Hz, 1H), 3.03 (s, 3H), 2.97 (m, 2H), 2.88 (m, 1H), 2.40 (dd, J=16.8, 5.4 Hz, 1H), 1.43 (s, 9H).

b) 8-[[2S-Amino-3-phenylpropanoyl]amino]-2-methyl-3-oxo-2,3,4,5-tetrahydro-1H-2-benzazepine-4RS-acetic acid Methyl-8-[[2S-(tert-butoxycarbonyl)amino-3-phenylpropanoyl]amino]-2-methyl-3-oxo-2,3,4,5-tetrahydro-1H-2-benzazepine-4(R,S)-acetate was deprotected according to the procedure of Example 20(b) to give the tide compound as a light yellow foam (58%): MS (ES) m/e 396(M+H)$^+$. Anal. Calcd for C$_{22}$H$_{25}$N$_3$O$_4$.1.57 C$_2$F$_3$HO$_2$: C, 52.56; H, 4.66; N, 7.73. Found: C, 52.95; H, 4.90; N, 6.92.

Example 16

Preparation of (±)-8-[[[(2-hydroxy-2-phenyl)ethyl]methylamino]carbonyl]-2-methyl-3-oxo-2,3,4,5-tetrahydro-1H-2-benzazepine-4-acetic acid a) Methyl (±)-8-[[[(2-hydroxy-2-phenyl)ethyl]methylamino]carbonyl]-2-methyl-3-oxo-2,3,4,5-tetrahydro-1H-2-benzazepine-4-acetate EDC (230 mg, 1.2 mmole) was added to a stirred solution of methyl (±)-8-carboxy-2-methyl-3-oxo-2,3,4,5-tetrahydro-1H-2-benzazepine-4-acetate (1.0 mmol), (±)-α-(methylaminomethyl)benzyl alcohol (1.2 mmol), HOBT.H$_2$O (162 mg, 1.2 mmol), and diisopropylethylamine (0.70 mL, 4.0 mmol) in anhydrous DMF (5 mL) at RT. After 19 hr, the reaction was concentrated on the rotavap (high vacuum), and the residue was partitioned between H$_2$O and EtOAc. The layers were separated and the organic layer was washed with H$_2$O. Drying (MaSO$_4$), concentration, and chromatography (silica gel, 1%–3% CH$_3$OH/CH$_2$Cl$_2$) gave the title compound as an off-white foam (62%): $^1$H NMR (CDCl$_3$) (mixture of diastereomers) δ8.62 (d, J=5 Hz), 8.29 (d, J=7.8 Hz), 7.93 (m), 7.81 (m), 7.62 (s), 7.45 (m), 7.18 (d, J=5 Hz), 7.11 (d, J=8.3 Hz), 7.00 (d, J=8.2 Hz), 5.42 (br s), 5.33 (d, J=16), 5.25 (d, J=16 Hz), 3.88 (d, J=16.5 Hz), 3.85 (m), 3.79 (d, J=16.3 Hz), 3.70 (s), 3.69 (s), 3.05 (s), 3.01 (s), 3.00 (m), 2.43 (m), 2.18 (s).

b) (±)-8-[[[(2-Hydroxy-2-phenyl)ethyl]methylamino]carbonyl]-2-methyl-3-oxo-2,3,4,5-tetrahydro-1H-2-benzazepine-4-acetic acid Methyl (±)-8-[[[(2-hydroxy-2-phenyl)ethyl]methylamino]carbonyl]-2-methyl-3-oxo-2,3,4,5-tetrahydro-1H-2-benzazepine-4-acetate was saponified according to the procedure of Example 6(b) to give the title compound as a white solid (80%): $^1$H NMR (DMSO-d$_6$) δ8.12 (m, 1H), 7.80 (m, 2H), 7.53 (m, 2H), 7.41 (m, 2H), 5.09 (m, 2H), 4.80 (m, 2H), 3.97 (m, 1H), 3.40 (m, 5H), 3.18 (s, 3H), 3.08 (m, 1H), 2.87 (m, 1H), 2.64 (m, 1H), 2.36 (m, 1H); MS (ES) m/e 411 (M+H)$^+$. Anal. Calcd for C$_{23}$H$_{26}$N$_2$O$_5$.1.75 H$_2$O: C, 62.50; H, 6.73; N, 6.34. Found: C, 62.60; H, 6.63; N, 6.19.

Example 17

Preparation of (±)-7-[[[N-(2-hydroxyethyl)-N-methyl]amino]carbonyl]-4-methyl-3-oxo-2,3,4,5-tetrahydro-1H-1,4-benzodiazepine-2-acetic acid a) Methyl (±)-7-[[[N-(2-hydroxyethyl)-N-methyl]amino]carbonyl]-4-methyl-3-oxo-2,3,4,5-tetrahydro-1H-1,4-benzodiazepine-2-acetate EDC (229.4 mg, 1.2 mmol) was added to a stirred solution of methyl (±)-7-carboxy-4-methyl-3-oxo-2,3,4,5- tetrahydro-1H-1,4-benzodiazepine-2-acetate (292.3 mg, 1.0 mmol), 2-(methylamino)ethanol (0.10 mL, 1.2 mmol), HOBT.H$_2$O (162.2 mg, 1.2 mmol), and diisopropylethylamine (0.35 mL, 2.0 mmol) in anhydrous DMF (5 mL) at RT. After 15.5 h, the reaction was concentrated on the rotavap (high vacuum), and the resulting yellow oil was dissolved in CHCl$_3$. The solution was washed with 10% Na$_2$CO$_3$, and the aqueous was back-extracted with CHCl$_3$. The combined organic layers were dried (Na$_2$SO$_4$), concentrated, and reconcentrated from xylenes to remove residual DMF. Chromatography (silica gel, 2:2:1 EtOAc/CHCl$_3$/MeOH) gave the title compound as a colorless oil (336 mg, 96%): TLC R$_f$ 0.46 (2:2:1 EtOAc/CHCl$_3$/MeOH); $^1$H NMR (250 MHz, CDCl$_3$) δ7.15–7.25 (m, 2H), 6.51 (d, J=8.9 Hz, 1H), 5.44 (d, J=16.4 Hz, 1H), 5.08 (t, J=6.6 Hz, 1H), 3.52–3.98 (m, 5H), 3.75 (s, 3H), 3.10 (s, 3H), 3.08 (s, 3H), 3.00 (dd, J=16.0, 6.8 Hz, 1H), 2.67 (dd, J=16.0, 6.4 Hz, 1H); IR (CHCl$_3$) 3060–3540, 1729, 1659, 1612, 1482, 1437, 1402 cm$^{-1}$; MS (ES) m/e 350.0 (M+H)$^+$.

b) (±)-7-[[[N-(2-Hydroxyethyl)-N-methyl]amino] carbonyl]-4-methyl-3-oxo-2,3,4,5-tetrahydro-1H-1, 4-benzodiazepine-2-acetic acid 1.0 N NaOH (1.4 mL, 1.4 mmol) was added dropwise to a solution of methyl (±)-7-[[[N-(2-hydroxyethyl)-N-methyl] amino]carbonyl]-4-methyl-3-oxo-2,3,4,5-tetrahydro-1H-1, 4-benzodiazepine-2-acetate (336.3 mg, 0.96 mmol) in MeOH (4.8 mL) at 0° C., and the resulting solution was stirred at RT. After 16 h, the reaction was concentrated, and the residue was purified by chromatography (ODS, 30% MeOH/H$_2$O). The fractions containing the product were combined. concentrated to dryness, and the residue was repurified by ODS chromatography (15% MeOH/H$_2$O). Concentration and lyophilization gave the title compound as a colorless powder (231 mg, 64%): HPLC k' 3.7 (PRP-1®, 10% CH$_3$CN/H$_2$O-0.1% TFA); $^1$H NMR (400 MHz, CD$_3$OD) δ7.11–7.20 (m, 2H), 6.59 (d, J=8.1 Hz, IH), 5.59 (d, J=16.5 Hz, 1H), 5.15 (t, J=7.0 Hz, 1H), 3.85 (d, J=16.5 Hz, 1H), 3.45–3.85 (m, 4H), 3.10 (br s, 3H), 3.03 (s, 3H), 2.79 (dd, J=15.5, 7.5 Hz, 1H), 2.45 (dd, J=15.5, 6.4 Hz, 1H); MS (ES) m/e 358.0 (M+Na)$^+$, 336.0 (M+H)$^+$. Anal. Calcd for C$_{16}$H$_{20}$N$_3$O$_5$Na.H$_2$O: C, 51.20; H, 5.91; N, 11.19. Found: C, 51.04; H, 6.04; N, 11.14.

Example 18

Preparation of (±)-8-[[(2-(2-pyridinylamino)acetyl] amino]-2-methyl-3-oxo-2,3,4,5-tetrahydro-1H-2-benzazepine-4-acetic acid a) Methyl 2-(2-pyridinyl)acetate hydrochloride A solution of 2-(2-pyridinyl)acetic acid (0.50 g, 3 mmol; prepared according to *J. Prakt. Chem.* 1961, 285, 118) in MeOH (20 mL) was saturated with HCl gas at 0° C., then was allowed to warm to RT. After stirring overnight, the reaction was concentrated under vacuum to afford the title compound (0.54 g, 100%) as a colorless solid: $^1$H NMR (CDCl$_3$) δ8.90 (br s, 1H), 7.89 (m, 2H), 6.89 (t, J=6.5 Hz, 1H), 6.79 (d, J=8 Hz, 1H), 4.21 (m, 2H), 3.81 (s, 3H).

b) Methyl 2-(N-tert-butoxycarbonyl-N-2-pyridinyl) aminoacetate

Methyl 2-(2-pyridinyl)aminoacetate hydrochloride (1.0 g, 5 mmol) was partitioned between EtOAc and 10% K$_2$CO$_3$. The organic layer was washed with brine, dried (MgSO$_4$), and concentrated. The residue was dissolved in CH$_2$Cl$_2$ (10 mL), and di-tert-butyl dicarbonate (1.2 g, 5 mmol) was added. The reaction was stirred at RT under argon overnight, then was concentrated. Chromatography on silica gel (1%–5% CH$_3$OH/CH$_2$Cl$_2$) gave the title compound as a pale yellow oil (0.89 g, 68%): $^1$H NMR (CDCl$_3$) δ8.31 (dd, J=4.8, 1.5 Hz, 1H), 7.84 (d, J=4.8 Hz, 1H), 7.67 (m, 1H), 7.00 (m, 1H), 4.73 (s, 2H), 3.75 (s, 3H), 1.52 (s, 9H).

c) 2-(N-tert-butoxycarbonyl-N-2-pyridinyl) aminoacetic acid

Methyl 2-(N-tert-butoxycarbonyl-N-2-pyridinyl) aminoacetate was saponified according to the procedure of Example 6(b) to give the title compound (74%) as a white solid.

d) Methyl (±)-8-[[2-(N-tert-butoxycarbonyl-N-2-pyridinyl)aminoacetyl]amino]-2-methyl-3-oxo-2,3,4, 5-tetrahydro-1H-2-benzazepine-4-acetate Methyl (±)-8-amino-2-methyl-3-oxo-2,3,4,5-tetrahydro-1H-2-benzazepine-4-acetate was coupled with 2-(N-tert-butoxycarbonyl-N-2-pyridinyl)aminoacetic acid according to the procedure of Example 5(b). Purification by silica gel chromatography (1%–3% CH$_3$OH/CH$_2$Cl$_2$) gave the title compound as a light yellow foam (56%): $^1$H NMR (CDCl$_3$) δ9.72 (s, 1H), 8.45 (d, J=4.2 Hz, 1H), 7.89 (t, J=4.2 Hz, 1H), 7.80 (d, J=8.3 Hz, 1H), 7.50 (s, 1H), 7.26 (m, 2H), 7.03 (d, J=8.4 Hz, 1H), 5.28 (d, J=16.4 Hz, 1H), 4.66 (s, 2H), 3.82 (d, J=16.4 Hz, 1H), 3.80 (m, 1H), 3.71 (s, 3H), 3.04 (s, 3H), 3.00 (m, 2H), 2.90 (m, 1H), 2.41 (dd, J=16.8, 5.2 Hz, 1H), 1.52 (s, 9H).

e) (±)-8-[[(2-(2-pyridinylamino)acetyl]amino]-2-methyl-3-oxo-2,3,4,5-tetrahydro-1H-2-benzazepine-4-acetic acid Methyl (±)-8-[[2-(N-tert-butoxycarbonyl-N-2-pyridinyl) aminoacetyl]amino]-2-methyl-3-oxo-2,3,4,5-tetrahydro-1H-2-benzazepine-4-acetate was deprotected according to the procedure of Example 20(b). Purification by chromatography (ODS, 10% CH$_3$CN/H$_2$O-0.1% TFA) followed by lyophilization gave the title compound as an off-white powder (23%): $^1$H NMR (CD$_3$OD) δ7.99 (m, 1H), 7.90 (d, J=6.4 Hz, 1H), 7.48 (d, J=2 Hz, 1H), 7.41 (dd, J=8.3, 2 Hz, 1H), 7.15 (d, J=9.2 Hz, 1H), 7.11 (d, J=8.4 Hz, 1H), 6.98 (m, 1H), 5.35 (d, J=16.4 Hz, 1H), 4.32 (s, 2H), 3.94 (d, J=16.4 Hz, IH), 3.90 (m, 1H), 3.07 (dd, J=17, 4.3 Hz, 1H), 2.70 (m, 2H), 2.45 (dd, J=17, 5 Hz, 1H); MS (ES) m/e 383.2(M+H)$^+$. Anal. Calcd for C$_{20}$H$_{22}$N$_4$O$_4$.1.5 C$_2$F$_3$HO$_2$0.5 H$_2$O: C, 49.11; H, 4.39; N, 9.96. Found: C, 49.23; H, 4.27; N, 10.07.

Example 19

Preparation of (±)-4-methyl-3-oxo-7-[[(2-phenylaminoethyl)amino]carbonyl]-2,3,4,5-tetrahydro-1H-1,4-benzodiazepine-2-acetic acid a) Methyl (±)-4-methyl-3-oxo-7-[[(2-phenylaminoethyl)amino]carbonyl]-2,3,4,5-tetrahydro-1H-1,4-benzodiazepine-2-acetate Following the procedure of Example 14(a), except substituting N-phenylethylenediamine for the 1-(2-pyrimidinyl) piperazine dihydrochloride, the title compound was prepared (78%): MS (ES) m/e 411 (M+H)$^+$.

b) (±)-4-Methyl-3-oxo-7-[[(2-phenylaminoethyl) amino]carbonyl]-2,3,4,5-tetrahydro-1H-1,4-benzodiazepine-2-acetic acid Following the procedure of Example 14(b), methyl (±)-4-methyl-3-oxo-7-[[(2-phenylaminoethyl)amino]carbonyl]-

2,3,4,5-tetrahydro-1H-1,4-benzodiazepine-2-acetate was saponified to give the title compound (24%): MS (ES) m/e 397 (M+H)$^+$. Anal. Calcd for $C_{21}H_{24}N_4O_4 \cdot 1.5$ $CF_3CO_2H \cdot 1.5$ $H_2O$: C, 48.49; H, 4.83; N, 9.42. Found: C, 48.41; H, 4.81; N, 9.40.

Example 20

Preparation of (±)-8-[(2-aminoacetyl)amino]-2-methyl-3-oxo-2,3,4,5-tetrahydro-1h-2-benzazepine-4-acetic acid a) Methyl (±)-8-[(2-[tert-butoxycarbonyl]aminoacetyl)amino]-2-methyl-3-oxo-2,3,4,5-tetrahydro-1H-2-benzazepine-4-acetate Methyl (±)-8-amino-2-methyl-3-oxo-2,3,4,5-tetrahydro-1H-2-benzazepine-4-acetate was coupled with Boc-glycine according to the procedure of example 5(b). Purification by chromatography (silica gel, 2%–5% $CH_3OH/CH_2Cl_2$) gave the title compound as a pale yellow foam (55%): $^1H$ NMR ($CDCl_3$) δ8.22 (br s, 1H), 7.48 (s, 1H), 7.20 (d, J=8.3 Hz, 1H), 7.04 (d, J=8.3 Hz, 1H), 5.27 (d, J=16.6 Hz, 1H), 5.25 (br s, 1H), 3.92 (d, J=5.4 Hz, 2H), 3.82 (m, 1H), 3.80 (d, J=16.6 Hz, 1H), 3.71 (s, 3H), 3.03 (s, 3H), 2.90 (m, 3H), 2.41 (dd, J=16.8, 5.5 Hz, 1H), 1.48 (s, 9H).

b) (±)-8-[(2-Aminoacetyl)amino]-2-methyl-3-oxo-2,3,4,5-tetrahydro-1H-benzazepine-2-acetic acid Methyl (±)-8-[(2-[tert-butoxycarbonyl]aminoacetyl)amino]-2-methyl-3-oxo-2,3,4,5-tetrahydro-1H-2-benzazepine-4-acetate was saponified according to the procedure of example 6(b). The resulting product was stirred in 1:1 $CH_2Cl_2$/TFA for 2 h, then was concentrated. Purification by chromatography (ODS, 10% $CH_3CN/H_2O$-0.1% TFA) followed by lyophilization gave the title compound as a white powder (76%): $^1H$ NMR (DMSO-$d_6$) δ8.10 (br s, 3H), 7.43 (d, J=8.2 Hz, 1H), 7.39 (s, 1H), 7.10 (d, J=8.2 Hz, 1H), 5.26 (d, J=16.1 Hz, 1H), 3.91 (d, J=16.1 Hz, 1H), 3.76 (m, 3H), 3.03 (dd, J=16, 2 Hz, 1H), 2.88 (s, 3H), 2.65 (m, 2H), 2.34 (dd, J=16, 2 Hz, 1H); MS (ES) m/e 306 (M+H)$^+$. Anal. Calcd for $C_{15}H_{19}N_3O_4 \cdot 1.5$ $C_2HF_3O_2 \cdot 0.5$ $H_2O$: C, 44.54; H, 4.47; N, 8.66. Found: C, 44.76; H, 4.47; N, 8.43.

Example 21

Preparation of (+/±)-8-[(3-aminopropanoyl)amino]-2-methyl-3-oxo-2,3,4,5-tetrahydro-1H-2-benzazepine-4-acetic acid a) Methyl (±)-8-[[3-[(tert-butoxycarbonyl)amino]propanoyl]amino]-2-methyl-3-oxo-2,3,4,5-tetrahydro-1H-2-benzazepine-4-acetate Methyl (±)-8-amino-2-methyl-3-oxo-2,3,4,5-tetrahydro-1H-2-benzazepine-4-acetate was coupled with Boc-β-alanine according to the procedure of Example 5(b). Purification by chromatography on silica gel gave the title compound (87%) as a light yellow foam: $^1H$ NMR ($CDCl_3$) δ8.20 (br s, 1H), 7.48 (s, 1H), 7.20 (d, J=8.3 Hz, 1H), 7.04 (d, J=8.3 Hz, 1H), 5.27 (d, J=16.6 Hz, 1H), 3.92 (m, 3H), 3.80 (d, J=16.6 Hz, 1H), 3.70 (s, 3H), 3.01 (s, 3H), 2.90 (m, 5H), 2.48 (dd, J=16.8, 5.5 Hz, 1H), 1.48 (s, 9H).

b) (±)-8-[(3-Aminopropanoyl)amino-2-methyl-3-oxo-2,3,4,5-tetrahydro-1H-2-benzazepine-4-acetic acid Methyl (±)-8-[[3-[(tert-butoxycarbonyl)amino]propanoyl]amino]-2-methyl-3-oxo-2,3,4,5-tetrahydro-1H-2-benzazepine-4-acetate was deprotected according to the procedure of Example 20(b). Purification by recrystallization ($CH_3OH$/EtOAc) gave the title compound as a white solid (45%): $^1H$ NMR (DMSO-$d_6$) δ7.47 (s, 1H), 7.37 (d, J=8.3 Hz, 1H), 7.03 (d, J=8.3 Hz, 1H), 5.23 (d, J=16.3 Hz, 1H), 3.85 (d, J=16.3 Hz, 1H), 3.70 (m, 1H), 2.98 (m, 2H), 2.87 (s, 3H), 2.65 (m, 3H), 2.30 (dd, J=16, 6.8 Hz, 1H); MS (ES) m/e 320 (M+H)$^+$. Anal. Calcd for $C_{16}H_{21}N_3O_4 \cdot 0.5$ $C_2F_3HO_2 \cdot 0.5$ $H_2O$: C, 52.37; H, 5.95; N, 10.78. Found: C, 52.29; H, 5.97; N, 10.78.

Example 22

Preparation of (±)-4-methyl-3-oxo-7-[[[(3-pyridinyl)methyl]amino]carbonyl]-2,3,4,5-tetrahydro-1H-1,4-benzodiazepine-2-acetic acid a) Methyl (±)-4-methyl-3-oxo-7-[[[(3-pyridinyl)methyl]amino]carbonyl]-2,3,4,5-tetrahydro-1H-1,4-benzodiazepine-2-acetate EDC (229.4 mg, 1.2 mmol) was added to a solution of methyl (±)-7-carboxy-4-methyl-3-oxo-2,3,4,5-tetrahydro-1H-1,4-benzodiazepine-2-acetate (292.3 mg, 1.0 mmol), 3-(aminomethyl)pyridine (0.122 mL, 1.2 mmol), HOBT·$H_2O$ (162.2 mg, 1.2 mmol), and diisopropylethylamine (0.35 mL, 2.0 mmol) in anhydrous DMF (5 mL) at RT. After 23.5 h, the reaction was concentrated on the rotavap (high vacuum), and the residue was partitioned between 10% aqueous $Na_2CO_3$ and $CHCl_3$. This caused a solid to precipitate. The layers were separated and the aqueous layer was extracted exhaustively with $CHCl_3$ until all solids had dissolved. The combined $CHCl_3$ layers were diluted with $CHCl_3$, washed with 10% $Na_2CO_3$, dried (MgSO$_4$), and concentrated. Crystallization of the residue from EtOAc gave impure title compound. The mother liquors were concentrated, combined with the recrystallized residue and chromatographed (silica gel, 10% MeOH/$CHCl_3$). The title compound was obtained as a colorless solid (341 mg, 89%): TLC $R_f$ 0.37 (10% MeOH/$CHCl_3$); $^1H$ NMR (250 MHz, $CDCl_3$) δ8.58–8.68 (m, 1H), 8.47–8.57 (m, 1H), 7.72–7.81 (m, 1H), 7.54 (d, J=2.1 Hz, 1H), 7.45 (dd, J=8.5, 2.1 Hz, 1H), 7.31 (dd, J=7.7, 4.8 Hz, 1H), 6.44–6.63 (m, 2H), 5.45 (d, J=16.4 Hz, 1H), 5.04–5.15 (m, 1H), 4.64 (d, J=5.9 Hz, 2H), 4.55 (br d, J=4.5 Hz, 1H), 3.76 (d, J=16.4 Hz, 1H), 3.75 (s, 3H), 3.07 (s, 3H), 2.99 (dd, J3=16.0, 6.7 Hz, 1H), 2.67 (dd, J=16.0, 6.4 Hz, 1H); MS (ES) m/e 383.2 (M+H)$^+$.

b) (±)-4-Methyl-3-oxo-7-[[[(3-pyridinyl)methyl]amino]carbonyl]-2,3,4,5-tetrahydro-1H-1,4-benzodiazepine-2-acetic acid A mixture of methyl (±)-4-methyl-3-oxo-7-[[[(3-pyridinyl)methyl]amino]-carbonyl]-2,3,4,5-tetrahydro-1H-1,4-benzodiazepine-2-acetate (161.7 mg, 0.42 mmol), 1.0 N NaOH (1.3 mL, 1.3 mmol), and MeOH (4.2 mL) was stirred at 40° C. for 3 h, then at RT overnight The resulting solution was concentrated, and the residue was dissolved in $H_2O$ and $CH_3CN$. The solution was acidified to pH 1 with TFA and was concentrated. The residue was crystallized from $H_2O$ to afford the title compound as an off-white, crystalline solid (120.9 mg, 60%): HPLC k' 5.7 (PRP-1®, 8% $CH_3CN/H_2O$-0.1% TFA); $^1H$ NMR (250 MHz, DMSO-$d_6$) δ8.60–8.83 (m, 3H), 8.15 (br d, J=8.0 Hz, 1H), 7.75 (dd, J=7.9, 5.3 Hz, 1H), 7.49–7.60 (m, 2H), 6.56 (d, J=9.1 Hz, 1H), 6.38 (br s, 1H), 5.49 (d, J=16.5 Hz, 1H), 5.01–5.16 (m, 1H), 4.37–4.65 (m, 2H), 3.82 (d, J=16.5 Hz, 1H), 2.92 (s, 3H), 2.77 (dd, J=16.7, 9.0 Hz, 1H), 2.61 (dd, J=16.7, 4.9 Hz, 1 H, partially obscured by the residual solvent signal); MS (ES) m/e 369.0 (M+H)+. Anal. Calcd for $C_{19}H_{20}N_4O_4 \cdot CF_3CO_2H$: C, 52.29; H, 4.39; N, 11.61. Found: C, 52.45; H, 4.40; N, 11.56.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

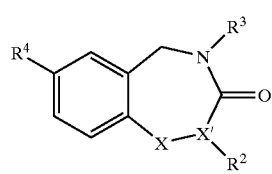

(I)

wherein

X—X' is $NR^1$—CH, $NC(O)R^3$—CH or N=C;

$R^1$ is H, $C_{1-6}$ alkyl or benzyl;

$R^2$ is $(CH_2)_nCO_2H$;

$R^3$ is H, $C_{1-6}$alkyl, Ar—$C_{0-6}$alkyl, Het-$C_{0-6}$alkyl, or $C_{3-6}$cycloalkyl-$C_{0-6}$alkyl;

$R^4$ is W—U;

$R^6$ is H, $C_{1-6}$alkyl, Ar—$C_{0-6}$alkyl, Het-$C_{0-6}$alkyl and $C_{3-6}$cycloalkyl-$C_{0-6}$alkyl;

n is 1 or 2;

U is $NR^1C(O)$, $C(O)NR^1$, CH=CH, C≡C, $CH_2$—$CH_2$, O—$CH_2$, $CH_2$—O or $CH_2OCONR^1$;

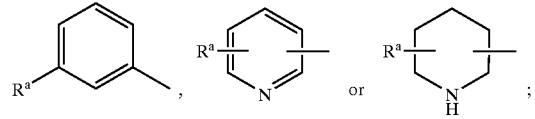

W is $R^a$ is H, OH, $NO_2$, $N(R^6)_2$, $CON(R^6)_2$, $CH_2N(R^6)_2$, or $R^6HN$—C(=NH);

and pharmaceutically acceptable salts thereof, provided that $R^3$ is not phenylethyl when $R^4$ is (3-amidino)phenylaminocarbonyl and X—X' is NH—CH.

2. A compound according to claim 1 which has a binding affinity to the vitronectin receptor relative to the fibrinogen receptor of greater than 3:1.

3. A compound according to claim 1 wherein X—X' is NH—CH and n is 1.

4. A compound according to claim 1 wherein U is $NR^1CO$.

5. A compound according to claim 1 wherein W is

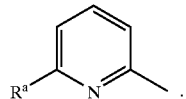

6. A compound of claim 1 selected from the group of:

(±)-7-[[(6-Amino-2-pyridinyl)amino]carbonyl]-4-methyl-3-oxo-2,3,4,5-tetrahydro-1H-1,4-benzodiazepine-2-acetic acid;

(±)-7-[[(6-amino-3-pyridinyl)amino]carbonyl]-3-oxo-4-(2-phenylethyl)-2,3,4,5-tetrahydro-1H-1,4-benzodiazepine-2-acetic acid;

(±)-1-Acetyl-7-[[(6-amino-2-pyridinyl)amino]carbonyl]-4-methyl-3-oxo-2,3,4,5-tetrahydro-1H-1,4-benzodiazepine-2-acetic acid;

(±)-7-[[[3-(aminoiminomethyl)phenyl]amino]carbonyl]-4-methyl-3-oxo-2,3,4,5-tetrahydro-1H-1,4-benzodiazepine-2-acetic acid;

(±)-7-[[[3-(aminocarbonyl)phenyl]amino]carbonyl]-4-methyl-3-oxo-2,3,4,5-tetrahydro-1H-1,4-benzodiazepine-2-acetic acid;

(±)-7-[[[N-(2-hydroxyethyl)-N-methyl]amino]carbonyl]-4-methyl-3-oxo-2,3,4,5-tetrahydro-1H-1,4benzodiazepine-2-acetic acid;

(±)-4-methyl-3-oxo-7-[[(2-phenylaminoethyl)amino]carbonyl]-2,3,4,5-tetrahydro-1H-1,4-benzodiazepine-2-acetic acid;

(±)-4-methyl-3-oxo-7-[[[(3-pyridinyl)methyl]amino]carbonyl]-2,3,4,5-tetrahydro-1H-1,4-benzodiazepine-2-acetic acid.

7. A pharmaceutical composition comprising a compound according to claim 1 and a pharmaceutically acceptable carrier.

8. A method for treating osteoporosis in a mammal comprising administering a compound according to claim 1 and a pharmaceutically acceptable carrier.

* * * * *